US012232944B2

(12) United States Patent
Dekeyser et al.

(10) Patent No.: US 12,232,944 B2
(45) Date of Patent: Feb. 25, 2025

(54) CHITOSAN TUBULAR MEMBER AND METHOD OF PRODUCING

(71) Applicant: CHECKPOINT SURGICAL, INC., Cleveland, OH (US)

(72) Inventors: Rachel Dekeyser, Cleveland, OH (US); Lisa Heller, Cleveland, OH (US); Ben Cottrill, Cleveland, OH (US); Derek Lewis, Cleveland, OH (US); Rachel Smith, Cleveland, OH (US)

(73) Assignee: CHECKPOINT SURGICAL, INC., Independence, OH (US)

( * ) Notice: Subject to any disclaimer, the term of this patent is extended or adjusted under 35 U.S.C. 154(b) by 0 days.

(21) Appl. No.: 18/684,712

(22) PCT Filed: Aug. 3, 2023

(86) PCT No.: PCT/US2023/029360
§ 371 (c)(1),
(2) Date: Feb. 19, 2024

(87) PCT Pub. No.: WO2024/044026
PCT Pub. Date: Feb. 29, 2024

(65) Prior Publication Data
US 2024/0325135 A1    Oct. 3, 2024

Related U.S. Application Data

(60) Provisional application No. 63/401,204, filed on Aug. 26, 2022.

(51) Int. Cl.
*A61F 2/00* (2006.01)

(52) U.S. Cl.
CPC .... *A61F 2/0063* (2013.01); *A61F 2002/0068* (2013.01); *A61F 2002/0072* (2013.01);
(Continued)

(58) Field of Classification Search
CPC ............ A61F 2/0063; A61F 2002/0068; A61F 2002/0072; A61F 2210/0014;
(Continued)

(56) References Cited

U.S. PATENT DOCUMENTS

| 5,695,857 A | 12/1997 | Burrell et al. |
| 8,337,386 B2 | 12/2012 | Li et al. |

(Continued)

FOREIGN PATENT DOCUMENTS

| CN | 100479785 | 4/2009 |
| CN | 107158467 | 9/2017 |

(Continued)

OTHER PUBLICATIONS

Patent Cooperation Treaty (PCT), International Search Report and Written Opinion for Application PCT/US2023/029360 filed Aug. 3, 2023, mailed Nov. 14, 2023, International Searching Authority, US.

(Continued)

*Primary Examiner* — Mohamed G Gabr
(74) *Attorney, Agent, or Firm* — McDonald Hopkins LLC

(57) ABSTRACT

Provided is a medical device formed entirely from or formed partially from a polymer, e.g., a polysaccharide such as chitosan. In some embodiments, the medical device may be formed as a tubular member formed from a sheet of a chitosan material. This chitosan tube may be used to wrap around tissue, such as a nerve or tendon to help with the regeneration or healing process of the nerve or tendon, as applicable.

54 Claims, 11 Drawing Sheets

(52) U.S. Cl.
CPC ............ *A61F 2210/0004* (2013.01); *A61F 2210/0014* (2013.01); *A61F 2210/0057* (2013.01); *A61F 2210/0061* (2013.01); *A61F 2210/0076* (2013.01); *A61F 2220/005* (2013.01); *A61F 2220/0075* (2013.01); *A61F 2230/0019* (2013.01); *A61F 2230/0026* (2013.01); *A61F 2230/0069* (2013.01); *A61F 2240/001* (2013.01); *A61F 2250/0036* (2013.01); *A61F 2250/0037* (2013.01); *A61F 2250/0039* (2013.01); *A61F 2250/0059* (2013.01)

(58) Field of Classification Search
CPC ...... A61F 2210/0057; A61F 2210/0061; A61F 2210/0076; A61F 2210/0004; A61F 2220/005; A61F 2220/0075; A61F 2230/0019; A61F 2230/0026; A61F 2230/0069; A61F 2240/001; A61F 2250/0036; A61F 2250/0037; A61F 2250/0039; A61F 2250/0059
See application file for complete search history.

(56) References Cited

U.S. PATENT DOCUMENTS

| | | | |
|---|---|---|---|
| 8,414,925 | B2 | 4/2013 | Freier |
| 9,801,978 | B2 | 10/2017 | Paulos et al. |
| 10,207,022 | B2 | 2/2019 | Montenegro et al. |
| 10,328,096 | B2 | 6/2019 | Freier |
| 2005/0042265 | A1 | 2/2005 | Guillot et al. |
| 2006/0286032 | A1 | 12/2006 | Ryu et al. |
| 2011/0311632 | A1 | 12/2011 | Roorda et al. |
| 2012/0059399 | A1* | 3/2012 | Hoke ............... A61B 17/1128 606/151 |
| 2013/0018454 | A1 | 1/2013 | Lelkes |
| 2013/0204078 | A1 | 8/2013 | Li et al. |
| 2014/0079686 | A1 | 3/2014 | Barman et al. |
| 2015/0216894 | A1 | 8/2015 | McCarthy et al. |

FOREIGN PATENT DOCUMENTS

| | | | |
|---|---|---|---|
| EP | 2159259 | A1 | 3/2010 |
| EP | 3266467 | A1 | 1/2018 |
| FR | 2848118 | A1 | 6/2004 |
| WO | 03068281 | A1 | 8/2003 |
| WO | 2008072230 | A1 | 6/2008 |
| WO | 2009056602 | A1 | 5/2009 |
| WO | 2016073723 | A1 | 5/2016 |

OTHER PUBLICATIONS

Ahmed, E., "Hydrogel: Preparation, characterization, and applications: A review," Journal of Advanced Research, Mar. 2015, vol. 6, Issue 2, pp. 105-121.

Chitosan Capsules OEM Europe, Datasheet [online], Tianjin Tianshi Biological Development Co. Ltd, 2017, [retrieved Mar. 8, 2024]. Retrieved from the internet: <URL:https://www.tiens-tianshi.com/chitosan-capsules-oem-europe.html>, 3 pages.

Extended European Search Report in EP17176184.4, mailed Sep. 4, 2017, 6 pages.

Intention to Grant EP17176184.4, mailed May 23, 2018, 1 page.

International Search Report in PCT/IB2020/054677, mailed Jul. 6, 2020, 5 pages.

Jordan et al., "Novel injectable urethral bulking agents for the treatment of urinary incontinence," Journal of Materials Science: Materials in Medicine, 2004, vol. 15, pp. 519-522.

Nakiri et al., "Bilateral Neurovascular Bundles Sparing Prostatectomy Preserves Sexual Function in Patients with Localized Prostate Cancer," Kurume Medical Journal, 2008, vol. 55, pp. 63-69.

Patel et al., "Dehydrated Human Amnion/Chorion Membrane Allograft Nerve Wrap Around the Prostatic Neurovascular Bundle Accelerates Early Return to Continence and Potency Following Robot-assisted Radical Prostatectomy: Propensity Score-matched Analysis," European Urology, Jun. 2015, vol. 67, Issue 6, pp. 977-980.

Piao et al., "Therapeutic Effect of Adipose-Derived Stem Cells and BDNF-immobilized PLGA Membrane in a Rat Model of Cavernous Nerve Injury," The Journal of Sexual Medicine, Aug. 2012, vol. 9, Issue 8, pp. 1968-1979.

Search Report and Written Opinion in IT201600070911, Mar. 10, 2017.

Text of EP17176184.4 for grant, Aug. 28, 2017, 29 pages.

Written Opinion in PCT/IB2020/054677, mailed Jul. 6, 2020, 6 pages.

* cited by examiner

The "Burrito" Technique. (A) Place the wrap underneath the target. (B) Fold one half of the wrap over onto the top of the target. Apply three drops of the setting solution. (C) Fold over the other half of the wrap before rinsing the area thoroughly.

CHITOSAN TUBULAR MEMBER AND METHOD OF PRODUCING

CROSS-REFERENCE TO RELATED APPLICATION

This application is a 35 U.S.C. § 371 national stage application of PCT Application PCT/US2023/029360 filed on Aug. 3, 2023 entitled "CHITOSAN TUBULAR MEMBER AND METHOD OF PRODUCING," which claims priority to U.S. Patent Application Ser. No. 63/401,204, filed on Aug. 26, 2022, and entitled "Chitosan Tubular Member and Method of Producing," each of which are incorporated herein by reference in their entireties.

FIELD OF INVENTION

The present invention relates generally to a tubular member formed from chitosan and, more specifically, a tubular member formed from chitosan to protect tissue during the healing process of the tissue.

BACKGROUND

Peripheral nerve injuries are diagnosed in 2.6% of upper extremity trauma patients and 1.2% of lower extremity trauma patients in the United States. The current "gold standard" treatment is use of a donor nerve from the patient (i.e., an autograft) to bridge the severed nerve ends. A procedure which is associated with a number of potential issues. These issues include the need for an additional surgery to harvest the donor material and the associated loss of function at the donor site. Alternatively, a donor nerve from a cadaver (i.e., an allograft) may be used, which may result in a size mismatch due to normal variation between individuals. At the implant site, both categories of donor nerves only serve as a guidance structure for the newly formed nerve tissue, without the transfer of any sensory function. Success rates are estimated at 50%. Moreover, due to the biological origin, the quality of donor tissue and thus the efficiency of nerve healing may vary, so that disturbed sensory functions or uncontrolled muscle contractions can result from inadequate nerve regeneration.

Synthetic nerve guides (e.g., nerve conduits, nerve wraps) were introduced as an alternative to nerve grafts. However, currently used conduits were shown to have issues in bridging distances of more than 5 mm compared to nerve grafts. Due to the non-biodegradability of materials used, long-term complications such as fibrosis and chronic nerve compression may occur, ultimately requiring that the conduits to be surgically removed. In the case of biodegradable or resorbable nerve guides, a rapid loss of mechanical strength due to fast degradation was observed with polyester- and collagen-based devices. This was also associated with the collapse of the conduits before completion of the nerve repair process as well as posing a risk of nerve compression.

Chitosan-based nerve guides represent a promising alternative to nerve grafts and synthetic devices in the treatment of injured peripheral nerves. Chitosan may provide bioactivity and may support nerve regeneration comparable to nerve grafts and without requiring an additional surgery and removal of a donor nerve. The degradation rate of chitosan can be adjusted to the clinical requirements. In addition, chitosan may allow for fabrication of collapse-stable nerve conduits that are resistant or less susceptible to undesirable collapse.

The polysaccharide chitosan is the N-deacetylated derivative of chitin, which can be found widely in the exoskeletons of arthropods, shells, and crustaceans, and in the cuticles of insects. Chitosan, although naturally occurring in some fungi, is produced industrially by alkaline hydrolysis of chitin. The different solubility of chitin and chitosan in dilute acids are commonly used to distinguish between the two polysaccharides. Chitosan, the soluble form, can have a degree of acetylation between 0% and about 60%, the upper limit depending on parameters such as processing conditions, molecular weight, and solvent characteristics.

Because of the biocompatibility, biodegradability, and structural similarity to the glycosaminoglycans, chitosan is a particularly promising polymer for biomedical applications. However, despite a great variety of potential applications, only a few chitosan products are currently in commercial use. One of the major limiting factors for a still broader utilization of chitosan is the difficulty in processing the polysaccharide into products having the desired shape.

U.S. Pat. No. 8,414,925 describes a process of manufacturing an article comprising N-acylchitosan hydrogel with a desired cross-sectional shape via an extrusion process comprising the steps of providing a mixture containing chitosan and/or N-acylchitosan, and extruding the mixture, wherein the article comprising N-acylchitosan hydrogel is a medical device selected from the group consisting of a tubular or fiber-based medical device, including a nerve guide. However, according to the process described in U.S. Pat. No. 8,414,925, the extrusion of chitosan into a tubular or fiber-based medical device requires several demanding processing steps including harsh chemical treatment in strong alkaline solution at high temperature, which can be difficult and expensive to do. Further, the described processes do not appear to produce a final tube having discrete longitudinal sections of varying thickness and/or formed in a mesh-like pattern.

It is desirable to provide a simple and efficient method for manufacturing a tubular chitosan medical product comprising a nerve guide, to avoid the need of harsh chemical treatment associated with the extrusion process.

In many indications a medical product may comprise a hollow body, such as a medical stent, the wall of the hollow body either being coated with, formed entirely from, or formed partially from a polymer, e.g., a polysaccharide such as chitosan.

SUMMARY

The present disclosure relates to a medical device formed entirely from or formed partially from a polymer, e.g., a polysaccharide such as chitosan. In some embodiments, the medical device may be formed as a tubular member formed from a sheet of a chitosan material. This chitosan tube or sleeve may be used to wrap around tissue, such as a nerve or tendon, to help with the regeneration or healing process of the nerve or tendon, as applicable.

In one series of aspects, a number of methods for repairing a nerve or tendon using a synthetic nerve guide comprising at least one chitosan sheet are contemplated. These methods include forming a biodegradable sheet from a composition including chitosan, said composition configured to dissolve within 1 to 21 months after the biodegradable sheet is formed: wrapping the biodegradable sheet around a mandrel having a preselected size and shape to form a synthetic nerve guide: and disposing the synthetic nerve guide around an injured nerve or tendon. The mandrel can have a square or oval cross-sectional shape, and it may be formed from a plurality of components so that: i) the components are disposed around the injured nerve or tendon prior to wrapping the mandrel, and ii) the components are removed after the synthetic nerve guide is formed.

Optionally, the wrapped mandrel may be placed in a forming shell before the synthetic nerve guide is formed or deployed/disposed around the nerve. In these aspects, the forming shell may have a textured finish along interfaces where the forming shell comes into physical contact with the wrapped mandrel and/or it may include axial sections configured to serve as couplers and/or reducers.

The foregoing methods may include one or more of the following steps and features, including various combinations thereof:
- disposing the wrapped mandrel is exposed to an alkaline medium for a selected period of time
- wherein the alkaline medium comprises methanol, water, and ammonia
- wherein a plurality of biodegradable sheets are wrapped around the mandrel sequentially or simultaneously
- wherein a portion of one or more of the biodegradable sheets do not overlap so as to create comparatively thinner and thicker axial sections along a length of the synthetic nerve guide
- wherein a single biodegradable sheet having a polygonal shape is wrapped around the mandrel so as to create comparatively thinner and thicker axial sections along a length of the synthetic nerve guide and wherein the polygonal shape is rectangular or trapezoidal.
- wherein the biodegradable sheet is a solid sheet and further comprising the step of perforating the solid sheet to form a mesh-like pattern prior to wrapping the biodegradable sheet around the mandrel.
- wherein the biodegradable sheet is formed from spaced apart fibers or strands configured to periodically overlap so as to create a mesh-like sheet.
- wherein the mesh-like sheet is formed by weaving or overlaying the fibers or strands in a helical pattern around the mandrel.
- disposing an adhering agent comprising methanol, water, and acetic acid onto the biodegradable sheet during or after the wrapping step.
- folding or wrapping at least one axial section of the wrapped biodegradable sheet prior to forming the synthetic nerve guide and, optionally, unfolding or unwrapping the axial section when the synthetic nerve guide is disposed around an injured nerve or tendon so as to extend an axial length of the synthetic nerve guide.
- dying or etching at least a portion of the biodegradable sheet prior to forming the synthetic nerve guide and, optionally, wherein the dying or etching includes creating a series of stripes, a grid, or a guide pattern to facilitate one or both of: wrapping the biodegradable sheet around the mandrel and disposing the synthetic nerve guide around the injured nerve or tendon.
- wherein the synthetic nerve guide is formed without any use of sutures.
- wherein the composition dissolves within 4 to 18 months after the biodegradable sheet is formed
- wherein the mandrel has an exposed outer surface consisting of polytetrafluoroethylene
- wherein the mandrel is split so as to have inner and outer tubes, with the biodegradable sheet wrapped around either the inner or the outer tube
- wherein the biodegradable sheet consists essentially of polysaccharides
- wherein the chitosan has between 0% and 60% acetylation Another method involves forming a chitosan tube comprises a chitosan film of pre-selected size and properties formed in a tubular shape around a cylinder (mandrel) of pre-selected diameter. During manufacture, the chitosan film is first brought into contact with a slightly acidic aqueous medium containing at least one organic solvent, and wherein the film is subsequently brought into contact with a slightly alkaline aqueous medium containing at least one organic solvent. The sheet is formed in a tube that is first 'glued' together with a solution that's made of methanol, water, and acetic acid. The fixation step that comes at the end involves a solution that's made of water, methanol, and ammonia.

A further method describes making a synthetic nerve guide comprising or consisting of chitosan. Here, the method involves preparing a liquid solution including a composition including chitosan and applying the liquid solution onto a tubular rod so that the solution adheres and solidifies around the rod to form a hollow, tubular chitosan layer, thereby creating a synthetic nerve guide. Notably, the composition is configured to dissolve within 1 to 21 months after the hollow, tubular chitosan layer is initially formed. Further iterations may include any one or combination of the following:
- wherein a plurality of hollow tubular chitosan layers are formed by sequentially applying the liquid solution onto the tubular rod.
- wherein at least portions of at least of the plurality of hollow, tubular chitosan layers overlap.
- wherein the overlap creates a variable thickness along an axial length of the synthetic nerve guide
- wherein the overlap creates a mesh-like structure including apertures in sidewalls of the hollow, tubular chitosan layer
- wherein the tubular rod consists of a braided or woven support structure selected to adhere chitosan thereto A separate set of aspects contemplates a synthetic nerve guide consisting of a hollow tubular body having woven or overlaid chitosan members spaced apart to create a mesh-like pattern: one or more longitudinal constraining members positioned over the mesh-like pattern: opposing, radially aligned coupling strands; and wherein the hollow tubular body, all of the longitudinal constraining members, and all of the coupling strands are configured to dissolve in between 1 and 21 months after the hollow tubular member is initially formed. Here, the chitosan members may be in the form of fibers or strands, while the coupling strands consist of sutures that may be threaded through loops formed in at least one terminal end of each longitudinal constraining member. Lastly, the hollow tubular body can have a varied radial diameter or shape along an axial length of the hollow tubular member.

A still further set of aspects involves a synthetic nerve guide comprising a hollow tubular member formed a biodegradable sheet including chitosan, said biodegradable sheet wrapped so as to overlap along at least an axially aligned portion of the hollow tubular member. This synthetic nerve guide does not include any sutures, and it is configured to dissolve in between 1 and 21 months after the hollow tubular member is initially formed. The biodegradable sheet can have a smooth surface except on an outermost exposed surface of the hollow tubular member, said outermost exposed surface having a textured finish.

Here, the hollow tubular member can be formed from one or a plurality of biodegradable sheets, with each sheet including chitosan and, more preferably, being of similar or identical composition. When multiple sheets are used, any one of combination of the following elements may be included:
- wherein the hollow tubular member includes a plurality of longitudinal sections and wherein at least two longitudinal sections have differing thicknesses.
- wherein there are at least three longitudinal sections, including two end sections and one midline section, and wherein the end sections have more layers than the midline section
- wherein there are at least two longitudinal sections, including an end section and a midline section, and wherein the midline section has more layers than the end section
- wherein at least two of the plurality of biodegradable sheets are adhered together with a composition including methanol, water, and acetic acid
- wherein a plurality of polygonal biodegradable sheets are wound together to form the hollow tubular member
- wherein at least two of the plurality of biodegradable sheets have different shapes
- wherein at least two of the plurality of biodegradable sheets have different longitudinal sizes When a single biodegradable sheet is used, the hollow tubular member can still have a stepped surface. In some of these aspects, the single biodegradable sheet is folded or wrapped to impart variable thickness along discrete longitudinal sections of the hollow tubular member.

Additionally, the biodegradable sheet(s) can be formed as a woven mesh or overlaid lattice of chitosan members, with the chitosan members spaced apart to define apertures in the hollow tubular member. In some of these aspects, longitudinal constraining members are provided and, further still, coupling members can be attached to the constraining members at one or both ends of the hollow tubular member.

DESCRIPTION OF THE DRAWINGS

Operation of the present teachings may be better understood by reference to the detailed description taken in connection with the following illustrations. These appended drawings form part of this specification, and written information in the drawings should be treated as part of this disclosure. In the drawings:

FIGS. 9A-9B are perspective illustrations of aspects of the tubular member or nerve wraps, including the formation thereof, in accordance with this disclosure, while

DETAILED DESCRIPTION

Figure 1:
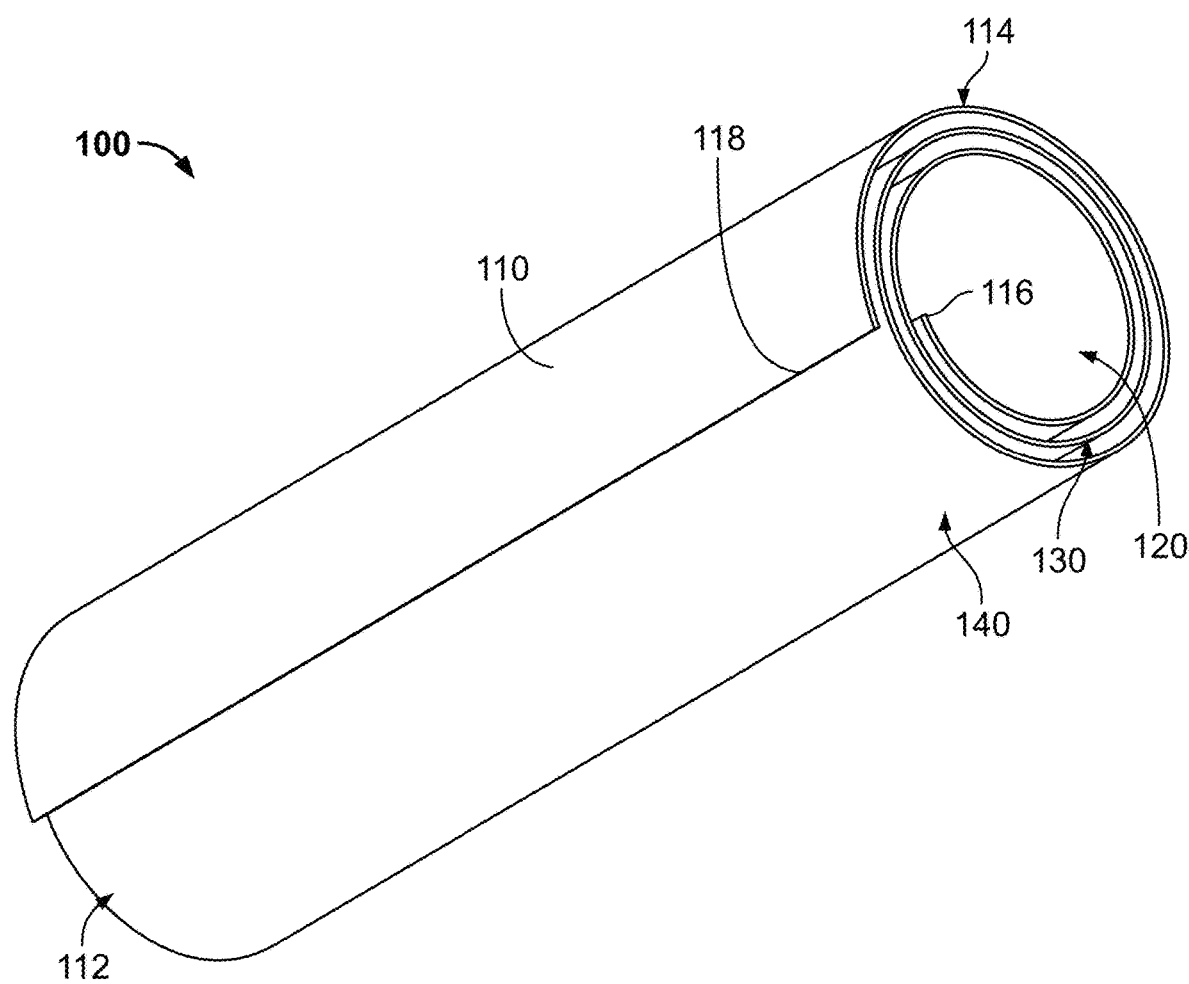
FIG. 1 is a perspective illustration of a first aspect of a tubular member or nerve wrap in accordance with this disclosure.

Reference will now be made in detail to exemplary embodiments of the present teachings, examples of which are illustrated in the accompanying drawings. It is to be understood that other embodiments may be utilized, and structural and functional changes may be made without departing from the respective scope of the present teachings. As such, the following description is presented by way of illustration only and should not limit in any way the various alternatives and modifications that may be made to the illustrated embodiments and still be within the spirit and scope of the present teachings.

As used herein, the words "example" and "exemplary" mean an instance, or illustration. The words "example" or "exemplary" do not indicate a key or preferred aspect or embodiment. The word "or" is intended to be inclusive rather an exclusive, unless context suggests otherwise. As an example, the phrase "A employs B or C," includes any inclusive permutation (e.g., A employs B: A employs C: or A employs both B and C). As another matter, the articles "a" and "an" are generally intended to mean "one or more" unless context suggests otherwise.

It is noted that the various embodiments described herein may include other components and/or functionality, such those from other described embodiments herein. It is further noted that while various embodiments refer to a medical device formed from chitosan, various other systems may be utilized in view of embodiments described herein. Further, the present system may include a variety of components, not limited to the components discussed below. Optionally, the present system may include multiple parts of the same components. In an embodiment, the present system may include just the chitosan tubular member described herein. Further, the present system may include components of each of the different embodiments of the chitosan tubular members described herein to create a combination of each feature of the various systems. Similarly, steps of producing a medical device, such as a nerve wrap, are disclosed. These steps may be done in a different order from what is disclosed, steps could be skipped and steps could be added without departing from the present teachings. Moreover, a step or steps from different embodiments of methods of forming the medical device may be combined with other embodiments to form a medical device having a different embodiment.

The present disclosure relates to an implantable medical device formed entirely from or formed partially from a polymer, e.g., a polysaccharide including, without limitation, chitosan. In some embodiments, the medical device may be formed as a tubular member formed from a sheet of a chitosan material or from one or more (or a plurality of) sheets or strips. This chitosan tubular member may be used to wrap around tissue, such as a nerve or tendon, to help with the regeneration or healing process of the nerve or tendon, as applicable. Once the chitosan tubular member has been wrapped around the applicable tissue, it may remain wrapped around such and will dissolve through time. In an example, the chitosan tubular member may dissolve from 1-21 months, 4-18 months, or any range therein. The time to dissolve may be manipulated or individualized by the thickness of the tubular member, a coating, or similar, and may be targeted to the needs and biology of the individual patient.

Chitosan, the soluble form, can have a degree of acetylation between 0% and about 60%, the upper limit depending on parameters such as processing conditions, molecular weight, and solvent characteristics. Manipulating the degree of acetylation of the chitosan can drive degradation rate.

A chitosan tube may be utilized in accordance with the following process. The chitosan tube may be utilized to wrap around a nerve, tissue, tendon, or the like to be part of the nerve or tendon tissue regeneration/healing process. In this situation, the chitosan tube may be placed over the injured nerve, such as a situation in which one nerve end is being attached to another nerve end or connected by an autograft. In these cases, the chitosan tube may be placed over the injured part of the nerve or the location at which the two nerves are attached. The chitosan in the chitosan tube may help accelerate the healing process of the nerve. In this case, the chitosan membrane favors Schwann cell infiltration and proliferation but prevents fibroblast infiltration and proliferation, which leads to the acceleration in healing of the nerve, tissue, tendon, or the like. Moreover, chitosan has anti-inflammatory properties, as it initiates an M2 macrophage response, as well as antimicrobial properties. These combination of features and benefits of chitosan result in an improved medical device to accelerate healing of tissues.

According to the present teachings, a method for manufacturing a chitosan medical product comprising a nerve guide, wherein a chitosan film of pre-selected size and properties is formed in a tubular shape around a cylinder (mandrel) of pre-selected diameter. During manufacture, the chitosan film is first brought into contact with a slightly acidic aqueous medium containing at least one organic solvent, and wherein the film is subsequently brought into contact with a slightly alkaline aqueous medium containing at least one organic solvent. In one embodiment, the sheet is formed in a tube that is first 'glued' together with a solution that's made of methanol, water, and acetic acid. The fixation step that comes at the end involves a solution that's made of water, methanol, and ammonia.

In one embodiment, the chitosan tube may be formed from a biodegradable sheet. The biodegradable sheet may be formed in any manner, including as disclosed in U.S. Pat. No. 10,328,096, which is incorporated herein by reference in its entirety. The chitosan sheet (e.g. forming tube 900 in FIGS. 9A and 9B) may be wrapped around a mandrel (e.g. 920 and/or 925 in FIGS. 9A and 9B) that is of the size of the interior diameter of the desired finished chitosan tube (see biodegradable sheet 600 and patterning 605, for example). In one embodiment, the mandrel may be formed from Teflon, but the present disclosure isn't limited to just this material and may be formed from any appropriate material. Once wrapped, the combined chitosan sheet and mandrel may be inserted into a forming shell such as a second tube (e.g. 910 in FIGS. 9A and 9B), typically a tube formed from polystyrene or any other tube of an appropriate material. It is noted that the forming shell may not necessarily have a tube shape, but may also include non-cylindrical shapes like cones, couplers, reducers, etc. This combination of the forming shell and mandrel is used to form the desired chitosan tube from e.g., a chitosan sheet. The mandrel and the chitosan sheet are inserted into the forming shell to prevent the chitosan tube from unwrapping. Moreover, the forming shell may help with the formation of the chitosan tube—it can provide a smooth or desired textured finish (see sheet 600 and patterning 605, for example) to the outer diameter of the chitosan tube. Advantageously, the forming shell only imparts the textured finish to the outer exposed layers, thereby allowing any inner, wrapped layers to retain a smooth finish which can improve adhesion along those smooth, interior surfaces.

Figure 9A:
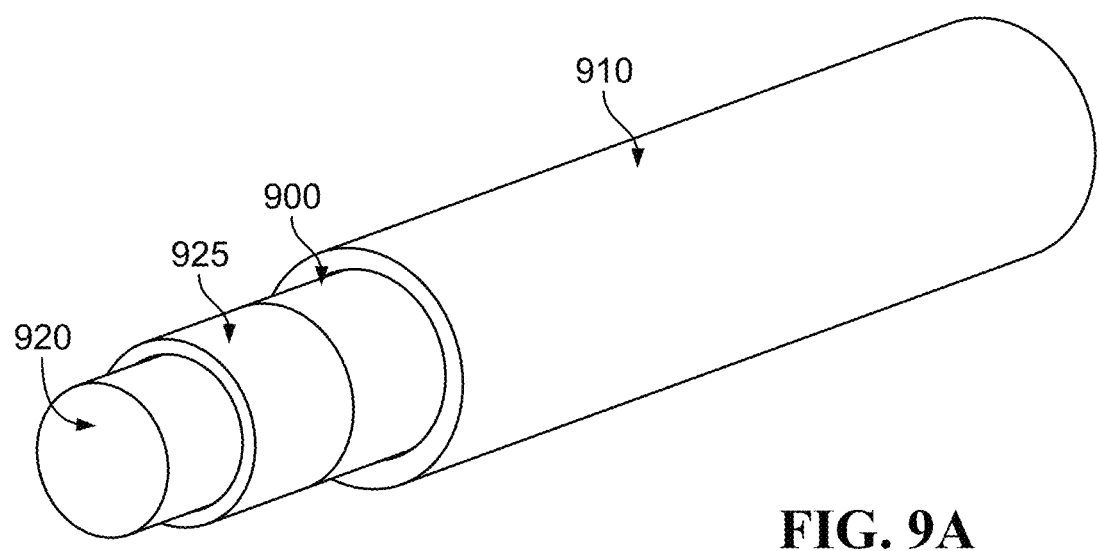
Figure 9B:
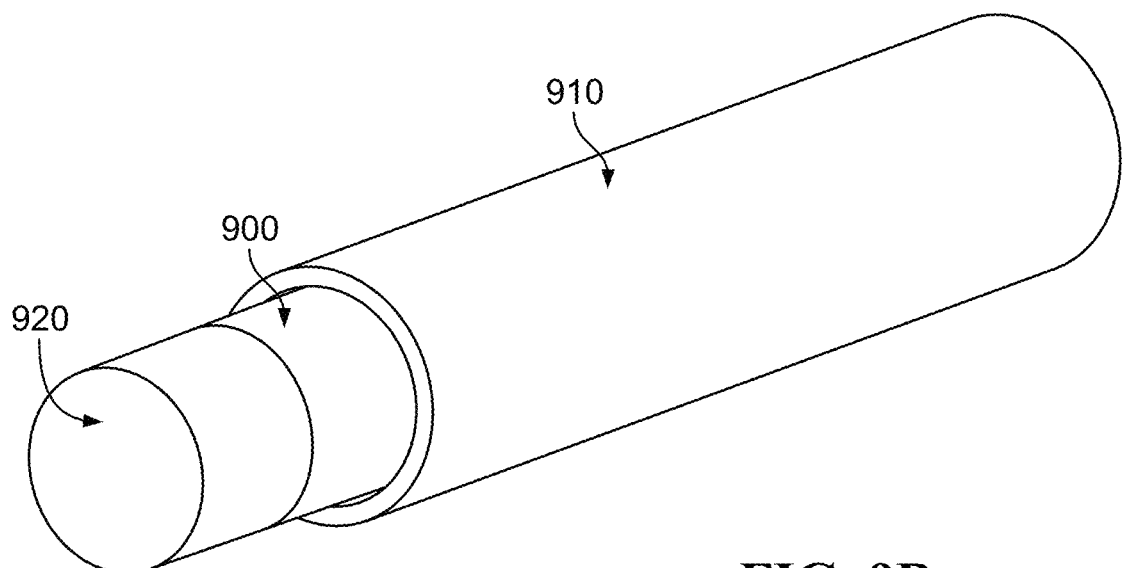
Figure 9C:
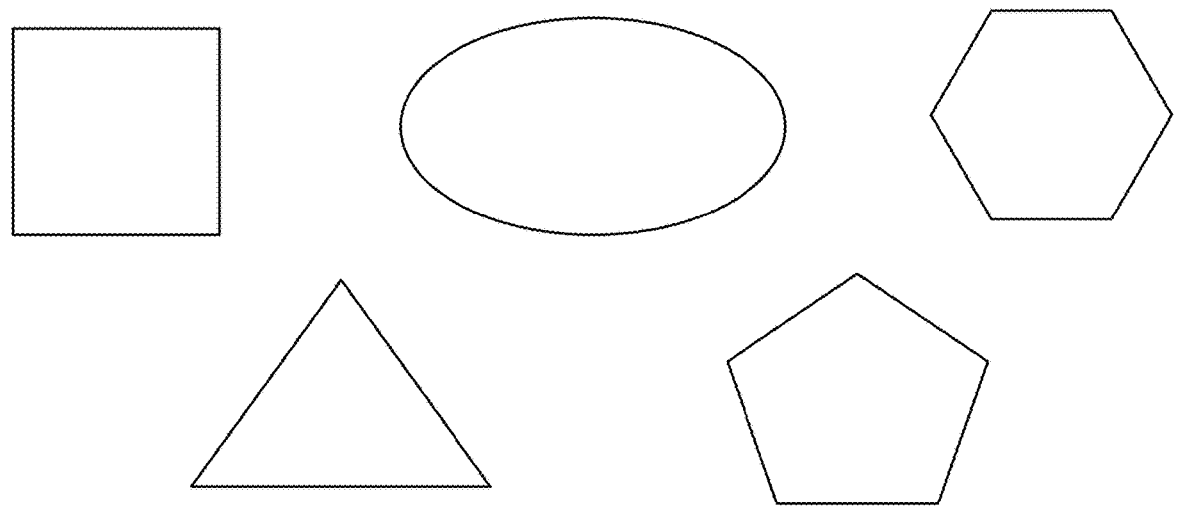
FIG. 9C is schematic illustration that is representative of the alternative cross-sectional shapes for the mandrel and resultant tubular member according to various disclosed aspects (including, without limitation, triangular, oval, square, pentagonal, and other polygonal shapes)

FIGS. 9A and 9B show an example of a chitosan material 900 formed into a tube, surrounded by a forming shell such as a second tube 910, and having a cross-sectionally circular mandrel 920 and optionally a mandrel component 925 inserted therein. FIG. 9C shows examples of alternative cross sectional shapes the mandrel may take, and it is understood that the mandrel can be provided as a one piece solid rod or hollow tube or that it may be two or multiple pieces that can be selectively coupled together. The mandrel 920 (and optionally 925) and the forming shell or second tube 910 may comprise a forming assembly. Mandrel 920 and mandrel component 925 may be referred to as the inner 920 and outer 925 mandrel components. It is noted that either or both the inner mandrel 920 and the outer mandrel 925 may be used herein as a part of the forming assembly. It is noted that mandrel 920 may be provided as one component shown in FIG. 9B or as more than one component 920/925, an example of which is shown in FIG. 9A.

The combined chitosan sheet and forming assembly may be inserted into an alkaline aqueous medium containing at least one organic solvent. In one embodiment, the forming shell may be removed during insertion into the alkaline medium. The organic solvent may comprise methanol, water, and ammonia. In some embodiments, the chitosan tube may be exposed to the alkaline solution for between one hour and forty-five minutes and two hours and fifteen minutes, e.g., about two hours. This can be accomplished in any appropriate manner. For example, a plurality of chitosan sheets and mandrels may be inserted into a large container of the aforementioned bath to form a plurality of chitosan tubes. This can also be done via a small batch or on an individual basis.

In some embodiments, the forming shell of the forming assembly may include a die with a predetermined form on it. This predetermined form may be engraved into the outer shell of the mandrel. When the chitosan tube is formed, this engraved outer shell may form a pattern in the chitosan tube, see patterning 605 on biodegradable sheet 600 in FIG. 6, which may represent an unfolded forming shell or second tube, or an unfolded chitosan tube already having a patterned inlayed.

Once the chitosan tube is formed, additional features may be added to it. These additional features may comprise flaps to allow flex. Perforations may be added to force a tear at a predefined area. In some embodiments, a slit may run along a majority portion of a length of the tube or the entire length of the tube to allow placement over an intact or repaired nerve. Any perforations or slits can be formed as part of the sheet, imparted as the tube is released from the mandrel and/or shell, or after the tube is fully formed.

Figure 10:
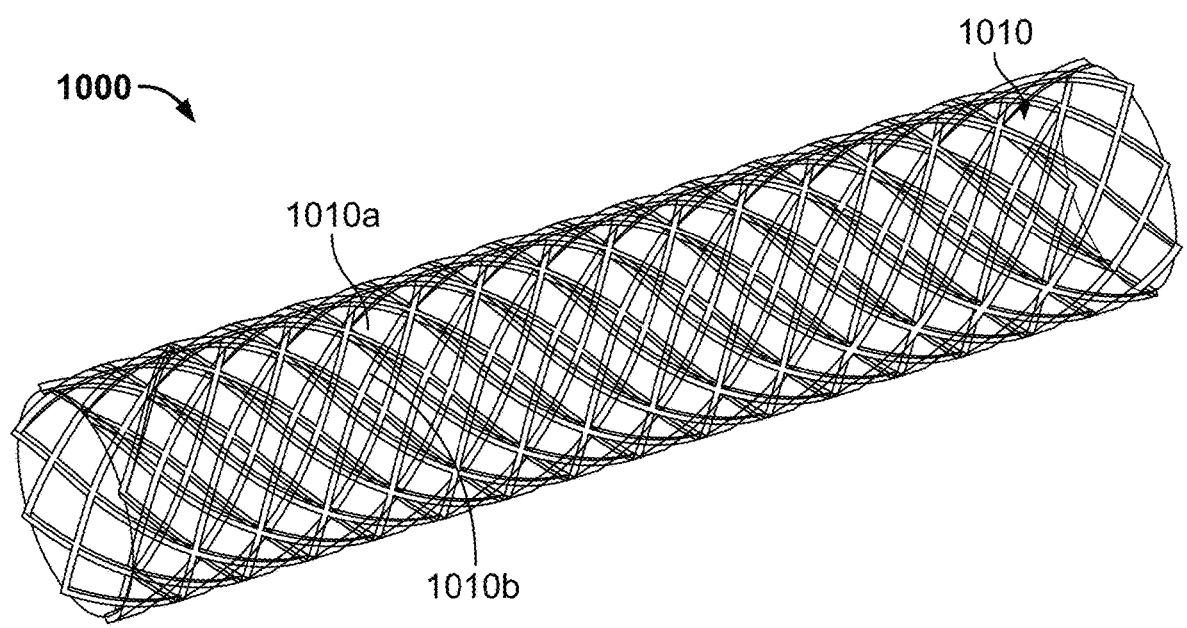
FIG. 10 is a perspective illustration of aspects of the tubular member or nerve wrap in accordance with this disclosure.

Additional features may similarly be added prior to forming the tube, e.g., when still in a sheet form. For example, a film may be used as the chitosan sheet to form the chitosan tube. For example, as shown in FIG. 10, the film may be provided with a plurality of holes to form a mesh or mesh or woven materials may be used in place of the film to form the chitosan tube 1000. In this aspect, a plurality of fibers 1010a, 1010b are laid or woven around the mandrel, preferably tracing a helical path around the mandrel so as to form a regular mesh-pattern. In this manner, the tubular surface 1000 (represented as a shaded area) is defined by the fibers 1010, 1010b along with the interstices therebetween. In another aspect, the sheet can be imparted or formed so as to have a mesh-pattern prior to winding around the mandrel.

Thus, strands of any appropriate material, including, without limitation, strips of chitosan, may be wound around the chitosan tube to further enhance and enforce the chitosan tube. The strands may be woven around the chitosan tube to enforce the chitosan tube. In these embodiments, the strands may be added to portions of the chitosan tube to enhance the final chitosan tube. By way of a non-limiting example, the chitosan strands may be added to portions of the chitosan tube to provide additional material to the end product, such as shown in FIG. 10. For example, to enhance the middle of the chitosan tube, the strands of chitosan may be added to the central portion of the chitosan tube. In addition, or alternatively, the strands of chitosan may be added to the ends of the chitosan tube to strengthen the ends or one of the ends of the chitosan tube.

Alternatively, the chitosan tube may itself be formed from strands of chitosan. In these embodiments, a tubular or rod forming device, similar to what is described above, may be used as a forming device whereby the strands of chitosan can be wrapped or woven around the tubular or rod forming device to form a tube of woven or wrapped chitosan. In an embodiment, the chitosan sheets can be wrapped independently, or a core may be temporarily inserted to mechanically support the chitosan tube during the wrapping process. Multiple layers of the chitosan strands may be wrapped around or woven together around the forming device. Once a first layer is put down, a solution of methanol, water, and acetic acid can be added to act as an adhering agent. Then, a second layer may be laid or positioned over the first layer. The solution of methanol, water, and acetic acid may then be adhered to the second layer. A third layer may then be placed over the second layer. This may be repeated until the applicable shape and size of the chitosan tube is formed. The resultant chitosan tube should be strong enough in construction, but such that it can have a core temporarily inserted to mechanically support the tube during the wrapping process.

In another alternative, strands of any appropriate material, including, without limitation, strips of chitosan, may first be wound or braided around a mandrel and then coated with a chitosan solution to fill the space between the fibers. In these embodiments, a tubular or rod forming device, similar to what is described above, may be used as a forming device whereby the strands of chitosan can be wrapped or woven around the tubular or rod forming device to form a tube of woven or wrapped chitosan.

A solution of chitosan (and/or polysaccharides) can also be applied to the rod or forming device using a brush, roller, sponge, by dripping onto the braid (this could comprise a slow drip), dipping into a bath of the chitosan solution (this could also comprise a slow dip), spraying, a combination of any of the foregoing or a similar process. This additive process may continue until the space between the fibers is filled to the specified thickness and the chitosan tube with specified dimension is formed. The resultant chitosan tube should be strong enough in construction, but such that it can have a core temporarily inserted to mechanically support the tube during the wrapping process. Alternatively, the rod or forming device could consist of a braided or woven structure, in which case one or more layers of chitosan adhere or attach to that support structure after it is brushed, rolled, sponged, dipped, dripped, etc.

Figure 11:
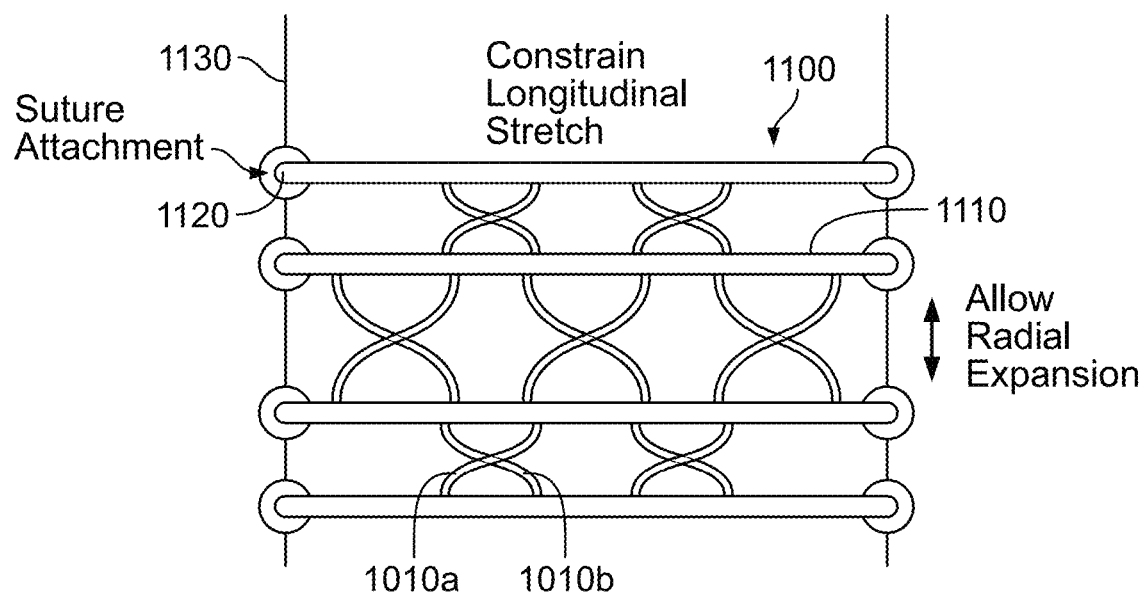
FIG. 11 is a schematic illustration of the construction and placement of aspects of the tubular member or nerve wrap in accordance with this disclosure.

The film can also be composed of a modified mesh. Prior to formation of the tube, a plurality of longitudinal features 1110 are interspersed within a mesh-like design (see FIG. 10). For example, as shown in FIG. 11, features 1120 are connected by mesh fibers 1010a, 1010b (as described above) to create a reinforced or modified mesh tube 1100. The ends of the features 1120 are coupled to a coupling suture 1130 or other similar carrier, possibly by passing the suture through an integrally formed loop at or near one or both terminal edges of the features 1120. The resultant structure is then wound around a mandrel to form the tubes contemplated in various aspects disclosed herein, or it can be formed on a removable carrier, such as split, two piece rod. The features 1120 can be laid down before or after the chitosan mesh members 1010a, 1010b are place on the mandrel, or the feature 1120 could be woven into the mesh. Preferably, the coupling suture 1130 is threaded, glued, or otherwise attached to the end(s) of the features 1120 at the same time or after the features 1120 are laid down. In one embodiment, one or both coupling sutures 1130 are pre-positioned so as to define the length of the sleeve, after which the resultant structure is wound around a mandrel to form the applicable tube, or it can be formed on a removable carrier, such as split, two piece rod.

Features 1120 and coupling suture 1130 can be formed from suitable suture materials, or other flexible and biocompatible materials, preferably having the same degrading characteristics as the base chitosan material. In some aspects, these features 1120, 1130 could be formed from chitosan. Further, coupling suture 1130 allow for radial expansion, while members 1120 constrain longitudinal stretching.

A chitosan tube, formed in accordance with any of the foregoing aspects, may be inserted into an alkaline aqueous medium containing at least one organic solvent. The organic solvent may comprise methanol, water, and ammonia. In some embodiments, the chitosan tube formed from the strands may be exposed to the alkaline solution or alkaline medium for between one hour and forty-five minutes and two hours and fifteen minutes, e.g., about two hours. The chitosan tubes may be formed on an individual basis or as part of a larger bath where multiple chitosan tubes may be formed at one time.

Turning to FIGS. 1-4, shown are various embodiments of a tubular member or nerve wrap. Although this disclosure may refer to a tubular structure, it is noted that this term is intended to include tube structures that have a circular (vertical) cross-section as well as other structures that may not necessarily have a circular (vertical) cross-section, but may have one or more flattened sides, an irregular or asymmetrical shape, a rectangular, pentagonal, hexagonal, etc., structure, and the like, unless context or this disclosure suggests otherwise, with a sampling of examples provided in FIG. 9C. It is further noted that the described tubular members may have a similarly shaped (vertical) cross-section or interior/exterior diameters across a length of the structure, or the tubular members may have increasing or decreasing interior diameters, exterior diameters, and/or (vertical) cross-sections having varied sizes or shapes across the length of the structure. In an embodiment, for example, the tubular member may be tapered, conical, frustoconical, and the like, or may have one or more flattened portions, sides, etc. Additionally, although this disclosure may refer to a nerve wrap, it is noted that this term may not be particularly limited to nerve applications per se, but may be used in the treatment of torn ligaments, tendons, etc. as well as in other biomedical applications. The use of the term "nerve" is generally used to provide context to a biomedical use of the tubular members unless context or this disclosure suggests otherwise.

FIG. 1 shows a first embodiment of a tubular member 100. Tubular member 100 may comprise a body 110 having a first end 112 and a second end 114 that is opposite the first end 112. Tubular member 100 may be formed from one or more pieces or sheets of material. In embodiments having more than one piece or sheet of material, it is noted that the additional pieces or sheets of material may be positioned adjacent the tubular member 100, on top or overlapping the tubular member 100, or a portion thereof, or a combination of the foregoing.

In an embodiment, tubular member 100 is formed from a single sheet of material. In an embodiment, tubular member 100 is formed from a single sheet of material having approximately four sides, e.g., two pairs of opposite sides having a generally equal length. In an embodiment, tubular member 100 is formed from a single sheet of material having an approximately rectangular shape. It is noted that other shapes are also disclosed and contemplated herein.

Figure 2:
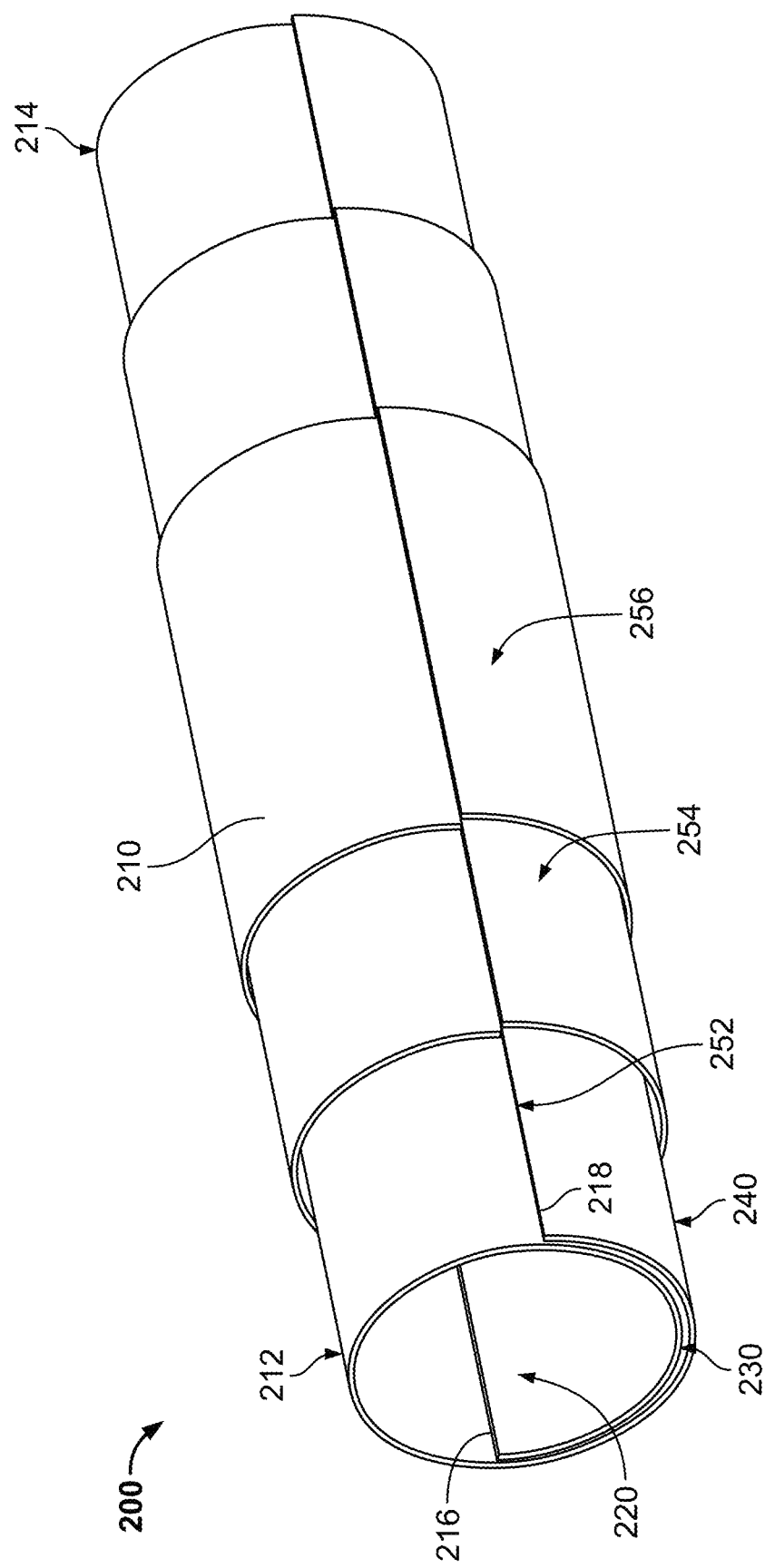
FIG. 2 is a perspective illustration of a second aspect of a tubular member or nerve wrap in accordance with various disclosed aspects herein.
Figure 3:
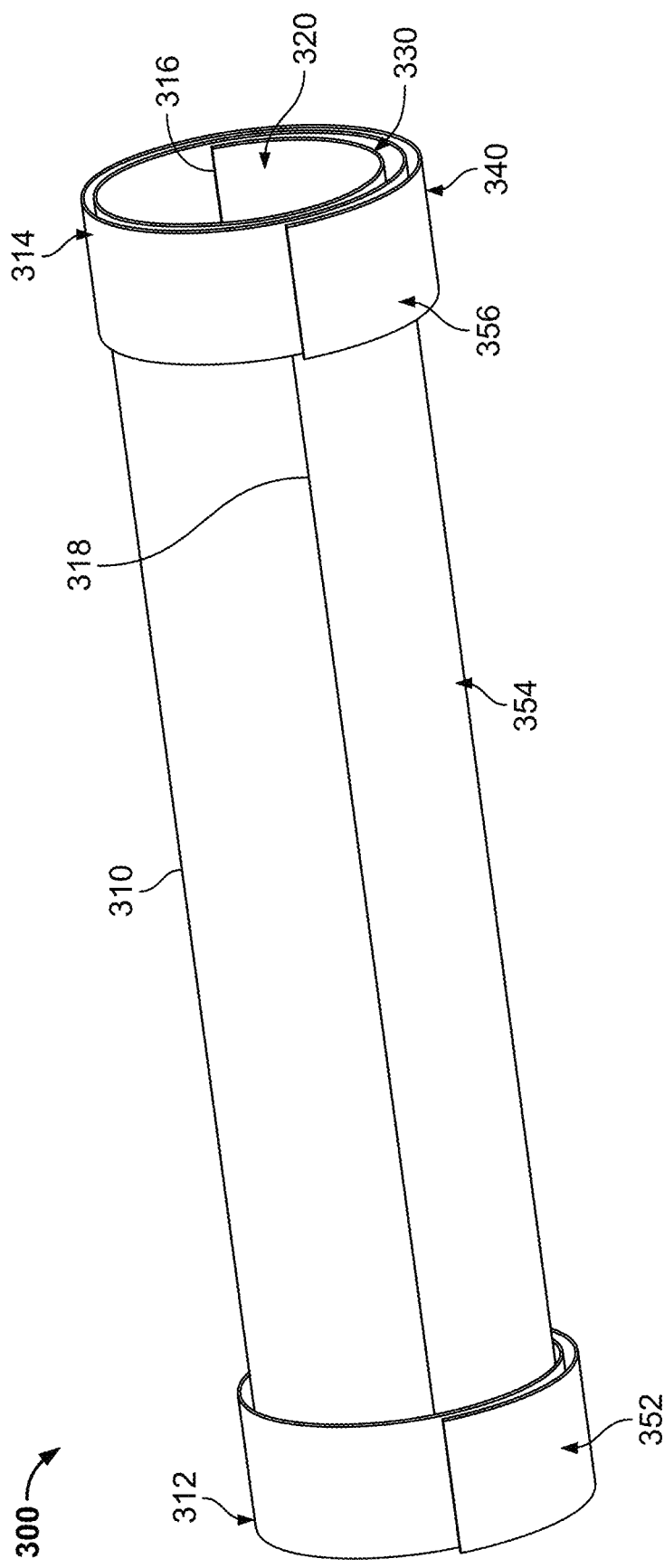
FIG. 3 is a perspective illustration of a third aspect of a tubular member or nerve wrap in accordance with this disclosure.
Figure 4:
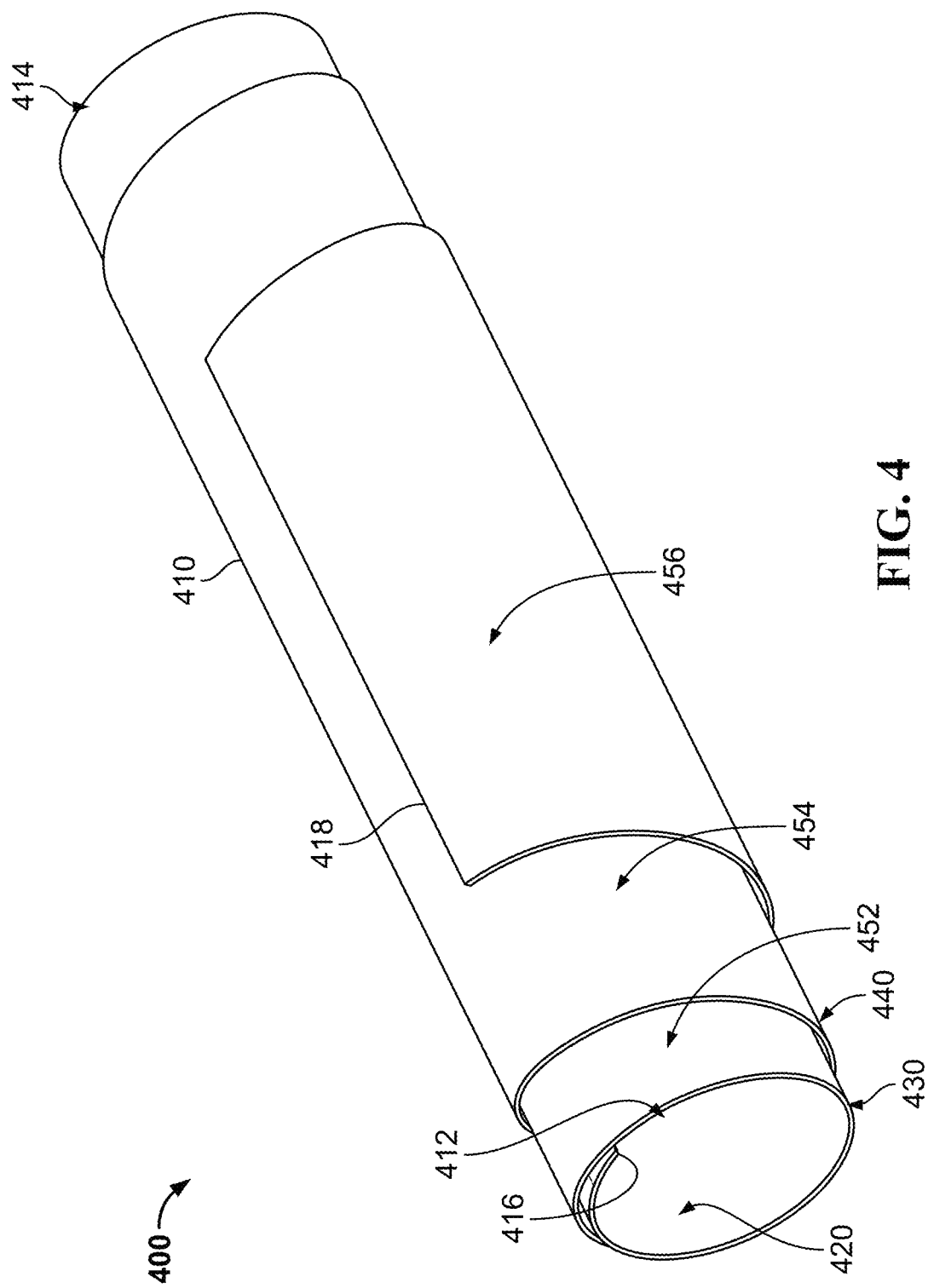
FIG. 4 is a perspective illustration of a fourth aspect of a tubular member or nerve wrap in accordance with this disclosure.
Figure 5:
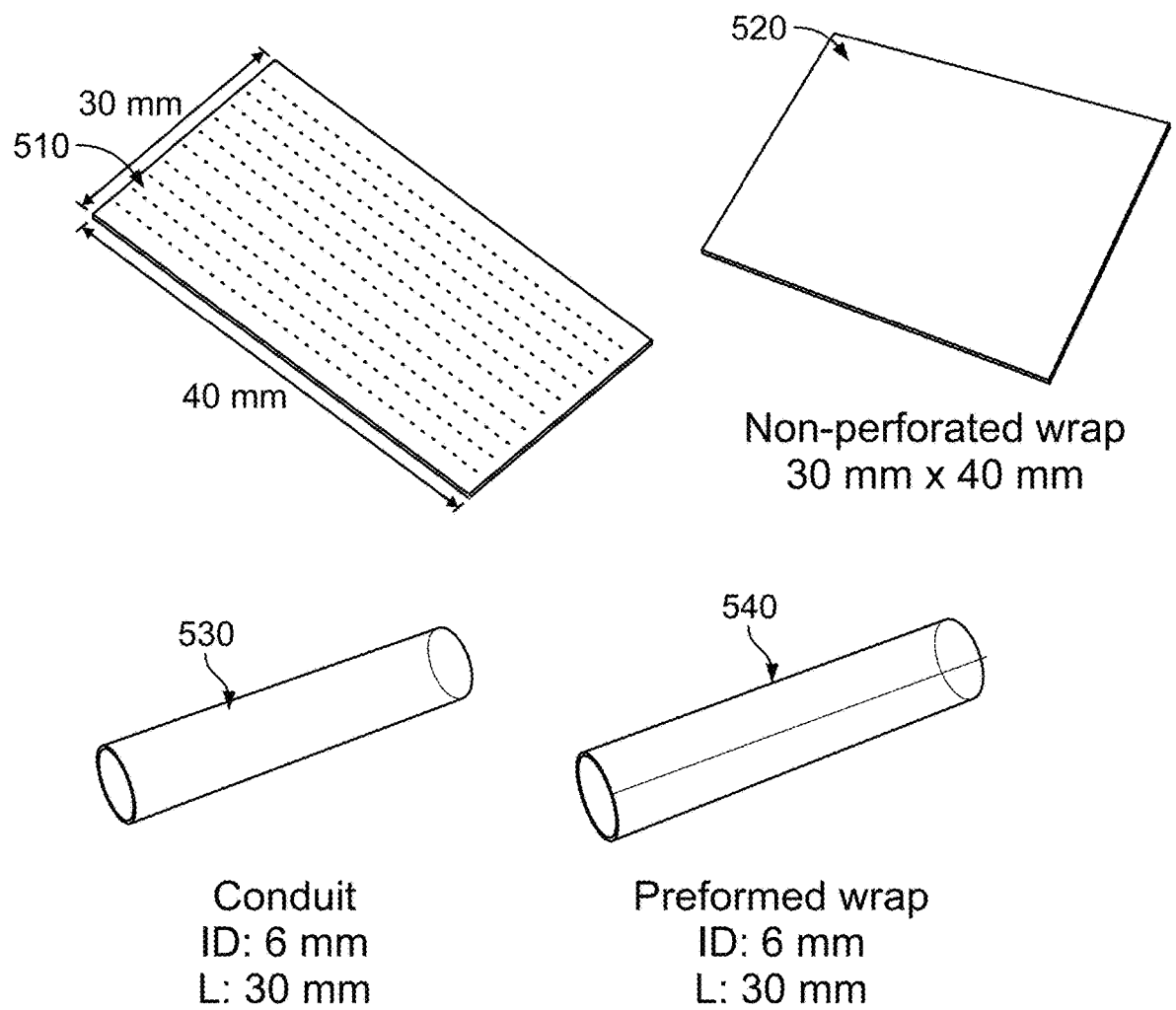
FIG. 5 is a schematic illustration highlighting the construction and assembly of a tubular member or nerve wrap in accordance with this disclosure.

It is noted that tubular member 100 is shown in FIG. 1 in a tube, "folded," or "wrapped" form, but that tubular member 100 may be provided in the form shown in FIG. 1 and may also be provided in a generally flat, "unfolded," or "unwrapped" form. Either the wrapped form or the unwrapped form may be manipulated or positioned around a desired target 5, e.g., nerve, tendon, ligament, or the like, to surround or partially surround the desired target 5. In a wrapped orientation, the tubular member 100 may generally comprise an interior cavity 120 of the tubular member formed by the wrapping of the body 110 into a wrapped position, one or more wrapped layers 130, and an exterior surface 140 of the tubular member 100 formed by the wrapping of the body 110 into a wrapped position. It is noted that the exterior surface 140 of the tubular member 100 may have a continuous "flat surface" as shown in FIG. 1, for example, or the exterior surface 140 of the tubular member 100 may have a "stepped surface" having a different number of layers as shown in FIGS. 2-4, for example. In this manner, the thinner sections would degrade more quickly than the thicker sections, allowing for sections of the tube to remain in place longer. This design may also allow for portions of the tube to degrade in a controlled manner.

In an embodiment, the first end 112 of the tubular member 100 may be opposite the second end 114 of the tubular member 100 on each side of the body 110. In an embodiment, the first end 112 may be approximately the same length as the second end 114. The first end 112 and the second end 114 may also correlate or refer to first and second sides, edges, or ends of the tubular member 100. In an embodiment, the first end 112 and the second end 114 may generally refer to the ends of the body 110 of the tubular member 100. In a wrapped position, the first end 112 and the second end 114 may generally refer to the open ends of the body 110 of the tubular member 100. The open ends, e.g., first and second ends 112, 114, may open into the interior 120 of the tubular member 100 and the open ends, e.g., first and second ends 112, 114, may be configured to receive a nerve, tendon, ligament, or the like therethrough. The first and second ends 112, 114 may be wider than the remaining portion of the tubular member 100. Specifically, an interior diameter of the first and second ends 112, 114 may by greater than an interior diameter of the remaining portion of the tubular member 100. This configuration may facilitate insertion of the nerve into the tubular member 100.

In an embodiment, tubular member 100 or body 110 of the tubular member 100 may comprise an interior edge 116 and an exterior edge 118. In an embodiment, the interior edge 116 may be approximately the same length as the exterior edge 118. The interior edge 116 and the exterior edge 118 may also correlate or refer to corresponding third and fourth sides, edges, or ends of the tubular member 100. In an unwrapped orientation, the interior edge 116 may be opposite the exterior edge 118. In a wrapped orientation, the interior edge 116 may be located in an interior (e.g., 120) of the tubular member 100 and the exterior edge 118 may be located on an exterior (e.g., 140) of the tubular member 100. The interior 120 of the tubular member 100 and the interior edge 116 may be configured to receive or contact a nerve, tendon, ligament, or the like therethrough.

As shown in FIG. 1, opposite sides and edges of the tubular member 100 may have generally the same length, e.g., opposite sides 112, 114 may have generally the same length and opposite edges 116, 118 may have generally the same length. In an embodiment, interior edge 116 may extend from the first end 112 to the second end 114 of the tubular member 100. In an embodiment, exterior edge 118 may extend from the first end 112 to the second end 114 of the tubular member 100. When in an unwrapped orientation, the tubular member 100 may resemble a rectangle. It is noted that other shapes are also disclosed and contemplated herein, including shapes having 3, 4, 5, 6, 7, etc. sides, shapes that have opposite sides of different lengths, shapes that are angled, shapes that have extended portions or irregular shapes, etc., for example, triangular, trapezoidal, diamond, parallelogram, and the like.

In an embodiment, the ends 112, 114 of the tubular member 100 may be flat, e.g., flat open ends. In an embodiment, a midline of the unwrapped sheet may generally align with or correspond to a midline of the wrapped tubular member 100. In an embodiment, each sequential wrap or layer of the tubular member 100 may align with the preceding wraps or layers. It is noted that other types of folds are wrapping are also disclosed and contemplated herein, including where each sequential wrap or layer is offset with preceding wraps or layers of the tubular member 100, where a midline of the unwrapped sheet may be offset from a midline of the wrapped tubular member 100, where the ends 112, 114 may not be flat or may be angled or tapered, etc.

In an embodiment, the body 110 and ends 112, 114 of the tubular member 100 may have generally the same vertical cross-section across its length. In an embodiment, the body 110 and ends 112, 114 of the tubular member 100 may have generally the same number of wraps or layers, e.g., 1, 2, 3, 4, 5, 6, etc. layers. In an embodiment, the body 110 and ends 112, 114 of the tubular member 100 may be generally uniform across its length, e.g., having the same interior 120 diameter, the same number of layers 130, and/or the same exterior 140 diameter across a length of the tubular member, including the body 110 and ends 112, 114. In an example, as shown in FIG. 1, the tubular member 100 may have all the same interior 120 diameter, the same number of layers 130, and/or the same exterior 140 diameter across a length of the tubular member 100, including the body 110 and ends 112, 114.

FIG. 2 shows a second embodiment of a tubular member 200. Tubular member 200 may comprise a body 210 having a first end 212 and a second end 214 that is opposite the first end 212. Tubular member 200 may be formed from one or more pieces or sheets of material. In embodiments having more than one piece or sheet of material, it is noted that the additional pieces or sheets of material may be positioned adjacent the tubular member 200, on top or overlapping the tubular member 200, or a portion thereof, or a combination of the foregoing.

In an embodiment, tubular member 200 is formed from a single sheet of material. In an embodiment, tubular member 200 is formed from a single sheet of material having approximately twelve sides, e.g., approximately three continuous sections (e.g., areas 252, 254, 256) having different sizes. In an embodiment, tubular member 200 is formed from a single sheet of material having approximately three continuous sections (e.g., areas 252, 254, 256) that sequentially increase or decrease in size or area. In an embodiment, tubular member 200 is formed from more than one sheet of material. In an embodiment, tubular member 200 is formed from three separate sheets (e.g., areas 252, 254, 256) of material having different sizes that are placed on top or overlapping each other (e.g., sequentially), or adjacent to each other. In an embodiment, tubular member 200 is formed from three separate sheets (e.g., areas 252, 254, 256) of material that sequentially increase or decrease in size or area and that are placed on top or overlapping each other (e.g., sequentially), or adjacent each other. Either or both of the three continuous sections or the three separate sheets of material (e.g., areas 252, 254, 256) may have generally rectangular shapes. It is noted that other shapes are also disclosed and contemplated herein.

Figure 7:
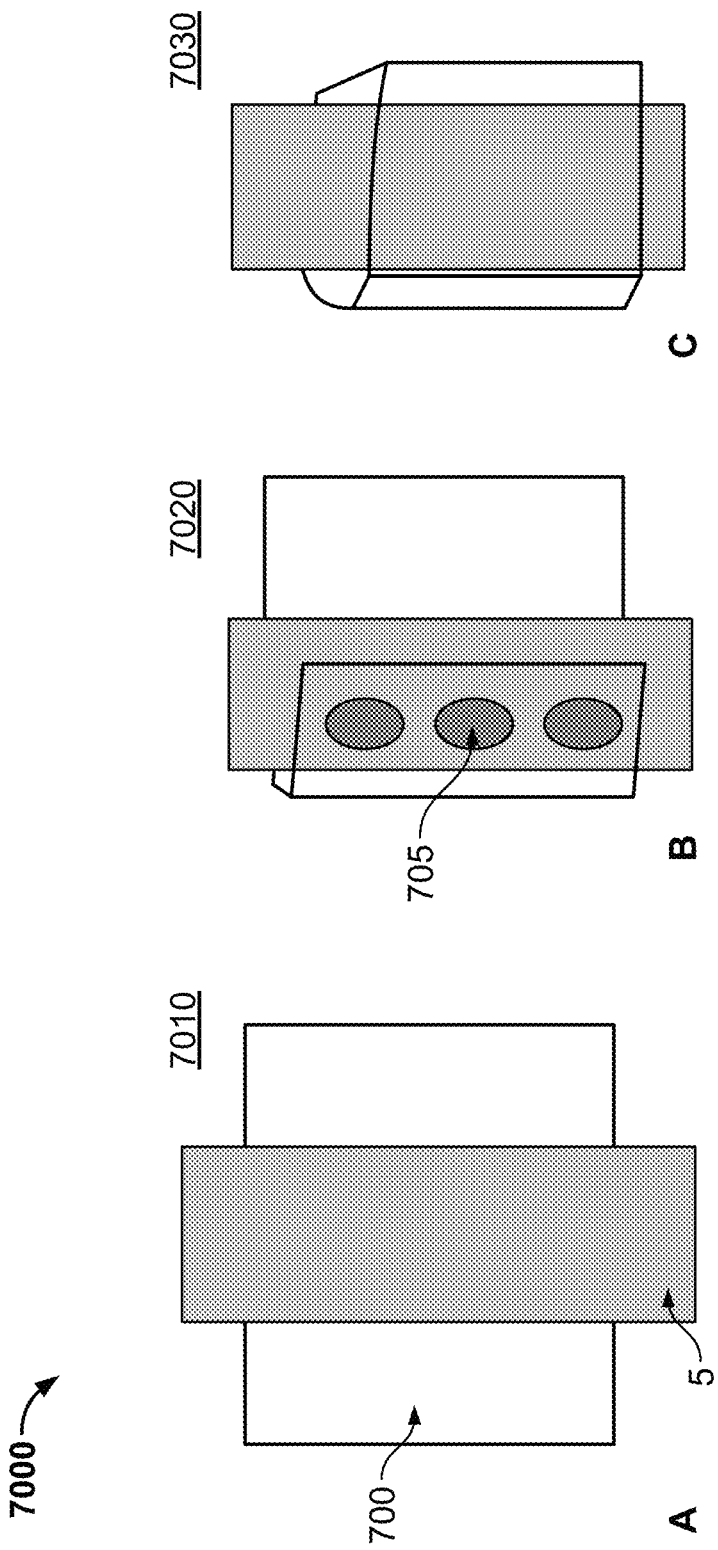
FIG. 7 is a sequential schematic view illustrating a method of applying a tubular member or nerve wrap to a target in accordance with this disclosure.

It is noted that tubular member 200 is shown in FIG. 2 in a tube, "folded," "wrapped," or closed form, but that tubular member 200 may be provided in the form shown in FIG. 2 and may also be provided in a generally flat, "unfolded," "unwrapped," or open form (see sheet 700 in step 7010 of FIG. 7, as an example). Either the wrapped form or the unwrapped form may be manipulated or positioned around a desired target 5, e.g., nerve, tendon, ligament, or the like, to surround or partially surround the desired target 5. In a wrapped orientation, the tubular member 200 may generally comprise an interior 220 of the tubular member formed by the wrapping of the body 210 into a wrapped position, one or more wrapped layers 230, and an exterior surface 240 of the tubular member 200 formed by the wrapping of the body 210 into a wrapped position. It is noted that the exterior surface 240 of the tubular member 200 may have a continuous "flat surface" as shown in FIG. 1, for example, or the exterior surface 240 of the tubular member 200 may have a "stepped surface" having a different number of layers as shown in FIGS. 2-4, for example.

In an embodiment, the first end 212 of the tubular body 200 may be opposite the second end 214 of the tubular member 200 on each side of the body 210. In an embodiment, the first end 212 may be approximately the same length as the second end 214. The first end 212 and the second end 214 may also correlate or refer to first and second sides, edges, or ends of the tubular member 200. In an embodiment, the first end 212 and the second end 214 may generally refer to the ends of the body 210 of the tubular member 200. In a wrapped position, the first end 212 and the second end 214 may generally refer to the open ends of the body 210 of the tubular member 200. The open ends, e.g., first and second ends 212, 214, may open into the interior 220 of the tubular member 200 and the open ends, e.g., first and second ends 212, 214, may be configured to receive a nerve, tendon, ligament, or the like therethrough.

In an embodiment, tubular member 200 or body 210 of the tubular member 200 may comprise an interior edge 216 and one or more exterior edges 218. The one or more exterior edges 218 may generally refer to the exterior edge(s) 218 exposed or formed on the exterior surface 240 when in a wrapped orientation and may be formed from multiple edges of a single sheet of material or may be formed from multiple edges of more than one sheet of material. As shown in FIG. 2, the tubular member 200 may be formed from multiple edges of multiple different sheets of material. These different sheets may help form the steps shown. In a non-limiting example as shown in FIG. 2, the tubular member 200 may be formed from three separate sheets that are rolled on top of one another starting from the widest sheet to the narrowest sheet (with an intermediate width sheet therebetween). An edge of each sheet may form the steps in the tubular member 200 shown. In an embodiment, the interior edge 216 may be approximately the same length as the one or more exterior edges 218. The interior edge 216 and the exterior edge 218 may also correlate or refer to corresponding sides, edges, or ends of the tubular member 200. In an unwrapped orientation, the interior edge 216 may be opposite the one or more exterior edges 218. In a wrapped orientation, the interior edge 216 may be located in an interior (e.g., 220) of the tubular member 200 and the one or more exterior edges 218 may be located on an exterior (e.g., 240) of the tubular member 200. The interior 220 of the tubular member 200 and the interior edge 216 may be configured to receive or contact a nerve, tendon, ligament, or the like therethrough.

As shown in FIG. 2 opposite sides and edges of the tubular member 200 may have generally the same length, e.g., opposite sides 212, 214 may have generally the same length and opposite edges 216, 218 may have generally the same (combined or net) length. In an embodiment, interior edge 216 may extend from the first end 212 to the second end 214 of the tubular member 200. In an embodiment, exterior edge(s) 218 may extend from the first end 212 to the second end 214 of the tubular member 200. When in an unwrapped orientation, the tubular member 200 may resemble three separate or continuous (e.g., depending on whether multiple sheets or a single sheet are used respectively) rectangular shapes. It is noted that other shapes are also disclosed and contemplated herein, including shapes having 3, 4, 5, 6, 7, etc. sides, shapes that have opposite sides of different lengths, shapes that are angled, shapes that have extended portions or irregular shapes, etc., for example, triangular, trapezoidal, diamond, parallelogram, and the like. Further, each of the sheets may have a different shape such that when overlaid a desired shape of a tubular member may be formed.

In an embodiment, the ends 212, 214 of the tubular member 200 may be flat, e.g., flat open ends. In an embodiment, a midline of the unwrapped sheet may generally align with or correspond to a midline of the wrapped tubular member 200. In an embodiment, each sequential wrap or layer of the tubular member 200 may align with the preceding wraps or layers. It is noted that other types of folds are wrapping are also disclosed and contemplated herein, including where each sequential wrap or layer is offset with preceding wraps or layers of the tubular member 200, where a midline of the unwrapped sheet may be offset from a midline of the wrapped tubular member 200, where the ends 212, 214 may not be flat or may be angled or tapered, etc.

In an embodiment, the tubular member 200 many generally include three sections 252, 254, 256 that correspond to three separate sheets or three continuous sections of a single sheet (e.g., depending on whether multiple sheets or a single sheet are used respectively). It is noted that other any number of sections are also disclosed and contemplated herein, including 1, 2, 4, 5, 6, 7, etc. sections. Each section may provide or form an additional wrap or layer. For example, the wrap formed from section 252 may have x number of layers, the wrap formed from section 254 may have x+y number of layers, and the wrap formed from section 256 may have x+y+z number of layers. In an embodiment, section 252 (having the least layers) may correspond to the first and second ends 212, 214 of the tubular member or the outer portions of the tubular member 200 and section 256 (having the most layers) may correspond to a middle portion or area of the body 210 of the tubular member 200. Section 254 may be located on each side of section 256 and in between sections 252 and 256. In an embodiment, the number of layers 230 of the tubular member 200 may increase from the outer ends (e.g., ends 212, 214) of the tubular member 200 towards the middle of the body 210 of the tubular member 200 and may decrease from a middle of the body 210 of the tubular member 200 to the outer ends (e.g., ends 212, 214) of the tubular body 200.

In an embodiment, the body 210 and ends 212, 214 of the tubular member 200 may have different vertical cross-sections across its length taken at sections 252, 254, 256. In an embodiment, the body 210 and ends 212, 214 of the tubular member 200 may have a different number of wraps or layers, e.g., 1, 2, 3, 4, 5, 6, etc. layers, at each section 252, 254, 256. In an embodiment, the body 210 and ends 212, 214 of the tubular member 200 may have a stepped outer surface 240 corresponding to sections 252, 254, 256. In an example, as shown in FIG. 2, the tubular member 200 may have all the same interior 220 diameter, a different number of layers 230 at sections 252, 254, 256, and the different exterior 240 diameter across a length of the tubular member 200, at sections 252, 254, 256.

FIG. 3 shows a third embodiment of a tubular member 300. Tubular member 300 may comprise a body 310 having a first end 312 and a second end 314 that is opposite the first end 312. Tubular member 300 may be formed from one or more pieces or sheets of material. In embodiments having more than one piece or sheet of material, it is noted that the additional pieces or sheets of material may be positioned adjacent the tubular member 300, on top or overlapping the tubular member 300, or a portion thereof, or a combination of the foregoing.

In an embodiment, tubular member 300 is formed from a single sheet of material. In an embodiment, tubular member 300 is formed from a single sheet of material having approximately eight sides, e.g., approximately three continuous sections (e.g., areas 352, 354, 356) having different sizes. In an embodiment, tubular member 300 is formed from a single sheet of material having approximately three continuous sections (e.g., areas 352, 354, 356) that include extended or longer end portions. In an embodiment, tubular member 300 is formed from more than one sheet of material. In an embodiment, tubular member 300 is formed from three separate sheets (e.g., areas 352, 354, 356) of material having different sizes that are placed on top or overlapping a preceding sheet, or adjacent each other. Either or both the three continuous sections or the three separate sheets of material (e.g., areas 352, 354, 356) may have generally rectangular shapes. It is noted that other shapes are also disclosed and contemplated herein.

It is noted that tubular member 300 is shown in FIG. 3 in a tube, "folded," "wrapped," or closed form, but that tubular member 300 be provided in this form shown in FIG. 3 and may also be provided in a generally flat, "unfolded," "unwrapped," or open form (see sheet 700 in step 7101 of FIG. 7, as an example). Either the wrapped form or the unwrapped form may be manipulated or positioned around a desired target 5, e.g., nerve, tendon, ligament, or the like, to surround or partially surround the desired target 5. In a wrapped orientation, the tubular member 300 may generally comprise an interior cavity 320 of the tubular member formed by the wrapping of the body 310 into a wrapped position, one or more wrapped layers 330, and an exterior surface 340 of the tubular member 300 formed by the wrapping of the body 310 into a wrapped position. It is noted that the exterior surface 340 of the tubular member 300 may have a continuous "flat surface" as shown in FIG. 1, for example, or the exterior surface 340 of the tubular member 300 may have a "stepped surface" having a different number of layers as shown in FIGS. 2-4, for example.

In an embodiment, the first end 312 of the tubular body 300 may be opposite the second end 314 of the tubular member 300 on each side of the body 310. In an embodiment, the first end 312 may be approximately the same length as the second end 314. The first end 312 and the second end 314 may also correlate or refer to first and second sides, edges, or ends of the tubular member 300. In an embodiment, the first end 312 and the second end 314 may generally refer to the ends of the body 310 of the tubular member 300. In a wrapped position, the first end 312 and the second end 314 may generally refer to the open ends of the body 310 of the tubular member 300. The open ends, e.g., first and second ends 312, 314, may open into the interior 320 of the hollow tubular member 300 and the open ends, e.g., first and second ends 312, 314, may be configured to receive a nerve, tendon, ligament, or the like therethrough.

In an embodiment, hollow tubular member 300 or body 310 of the tubular member 300 may comprise an interior edge 316 and one or more exterior edges 318. The one or more exterior edges 318 may generally refer to the exterior edge(s) 318 exposed or formed on the exterior surface 340 when in a wrapped orientation, and may be formed from multiple edges of a single sheet of material or may be formed from multiple edges of more than one sheet of material. In an embodiment, the interior edge 316 may be approximately the same length as the one or more exterior edges 318. The interior edge 316 and the exterior edge 318 may also correlate or refer to corresponding sides, edges, or ends of the tubular member 300. In an unwrapped orientation, the interior edge 316 may be opposite the one or more exterior edges 318. In a wrapped orientation, the interior edge 316 may be located in an interior (e.g., 320) of the tubular member 300 and the one or more exterior edges 318 may be located on an exterior (e.g., 340) of the tubular member 300. The interior 320 of the tubular member 300 and the interior edge 316 may be configured to receive or contact a nerve, tendon, ligament, or the like therethrough.

As shown in FIG. 3 opposite sides and edges of the tubular member 300 may have generally the same length, e.g., opposite sides 312, 314 may have generally the same length and opposite edges 316, 318 may have generally the same (combined or net) length. In an embodiment, interior edge 316 may extend from the first end 312 to the second end 314 of the tubular member 300. In an embodiment, exterior edge(s) 318 may extend from the first end 312 to the second end 314 of the tubular member 300. When in an unwrapped orientation, the tubular member 300 may resemble three separate or continuous (e.g., depending on whether multiple sheets or a single sheet are used respectively) rectangular shapes. It is noted that other shapes are also disclosed and contemplated herein, including shapes having 3, 4, 5, 6, 7, etc. sides, shapes that have opposite sides of different lengths, shapes that are angled, shapes that have extended portions or irregular shapes, etc., for example, triangular, trapezoidal, diamond, parallelogram, and the like.

In an embodiment, the ends 312, 314 of the tubular member 300 may be flat, e.g., flat open ends. In an embodiment, a midline of the unwrapped sheet may generally align with or correspond to a midline of the wrapped tubular member 300. In an embodiment, each sequential wrap or layer of the tubular member 300 may align with the preceding wraps or layers. It is noted that other types of folds and wrapping are also disclosed and contemplated herein, including where each sequential wrap or layer is offset with preceding wraps or layers of the tubular member 300, where a midline of the unwrapped sheet may be offset from a midline of the wrapped tubular member 300, where the ends 312, 314 may not be flat or may be angled or tapered, etc. In an embodiment, the tubular member 300 may comprise one end or two ends 312, 314 that have an internal diameter that is greater than the diameter of the remaining portion of the body of the tubular member 300. This configuration could similar to having two cones that are end-to-end such that the larger diameter ends extend away from one another and the narrower ends extend towards one another. This type of configuration can be utilized with any of the tubular members identified herein. The wider ends may aid in coaptation or nerve-end to nerve-end healing by allowing the two ends of the nerves to be inserted into the tubular member. The wider ends may allow the clinician to insert the nerve ends easier, i.e., it's easier to put the nerves into the wider openings and push them to the smaller diameter area to align them to heal appropriately.

In an embodiment, the tubular member 300 many generally include three sections 352, 354, 356 that correspond to three separate sheets or three continuous sections of a single sheet (e.g., depending on whether multiple sheets or a single sheet are used respectively). It is noted that other any number of sections are also disclosed and contemplated herein, including 1, 2, 4, 5, 6, 7, etc. sections. Each section may provide or form an additional wrap or layer. For example, the wrap formed from section 354 may have x number of layers, the wrap formed from section 352 may have x+y number of layers, and the wrap formed from section 356 may have x+z number of layers, where y and z may be the same number or different numbers. In an embodiment, sections 352, 356 (having more layers) may correspond to the first and second ends 312, 314 of the tubular member or the outer portions of the tubular member 300 and section 354 (having the least layers) may correspond to a middle portion or area of the body 310 of the tubular member 300. Section 352, 356 may be located on each side of section 354. In an embodiment, the number of layers 330 of the tubular member 300 may decrease from the outer ends (e.g., ends 312, 314) of the tubular member 300 towards the middle of the body 310 of the tubular member 300 and may increase from the middle of the body 310 of the tubular member 300 to the outer ends (e.g., ends 312, 314) of the tubular body 300.

In an embodiment, the body 310 and ends 312, 314 of the tubular member 300 may have different vertical cross-section across its length taken at sections 352/356 compared to section 354. In an embodiment, the body 310 and ends 312, 314 of the tubular member 300 may have a different number of wraps or layers, e.g., 1, 2, 3, 4, 5, 6, etc. layers, at sections 352/356 compared to section 354. In an embodiment, the body 310 and ends 312, 314 of the tubular member 300 may have a stepped outer surface 340 corresponding to sections 352, 354, 356. In an example, as shown in FIG. 3, the tubular member 300 may have all the same interior 320 diameter, a different number of layers 330 at sections 352/356 compared to section 354, and the different exterior 340 diameter across a length of the tubular member 300, at sections 352/356 compared to section 354.

FIG. 4 shows a fourth embodiment of a tubular member 400. Tubular member 400 may comprise a body 410 having a first end 412 and a second end 414 that is opposite the first end 412. Tubular member 400 may be formed from one or more pieces or sheets of material. In embodiments having more than one piece or sheet of material, it is noted that the additional pieces or sheets of material may be positioned adjacent the tubular member 400, on top or overlapping the tubular member 400, or a portion thereof, or a combination of the foregoing.

In an embodiment, tubular member 400 is formed from a single sheet of material—see FIG. 4. In an embodiment, tubular member 400 is formed from a single sheet of material having approximately four sides, e.g., approximately three continuous sections (e.g., areas 452, 454, 456) having different sizes. By way of a non-limiting example, the one sheet could be in the general shape of a rhombus (or similar such shape with variations). In an embodiment, tubular member 400 is formed from a single sheet of material having approximately three continuous sections (e.g., areas 452, 454, 456) that sequentially increase or decrease in size or area. In an embodiment, tubular member 400 is formed from more than one sheet of material. In an embodiment, tubular member 400 is formed from three separate sheets (e.g., areas 452, 454, 456) of material having different sizes that are placed on top or overlapping each other (e.g., sequentially), or adjacent to each other. In an embodiment, tubular member 400 is formed from three separate sheets (e.g., areas 452, 454, 456) of material that sequentially increase or decrease in size or area and that are placed on top or overlapping each other (e.g., sequentially), or adjacent each other. Either or both the single sheet of material or the three separate sheets of material (e.g., areas 452, 454, 456) may have generally trapezoidal shapes. It is noted that other shapes are also disclosed and contemplated herein.

It is noted that tubular member 400 is shown in FIG. 4 in a tube, "folded," "wrapped," or closed form, but that tubular member 400 be provided in this form shown in FIG. 4 and may also be provided in a generally flat, "unfolded," "unwrapped," or open form (see sheet 700 in step 7101 of FIG. 7, as an example). Either the wrapped form or the unwrapped form may be manipulated or positioned around a desired target 5, e.g., nerve, tendon, ligament, or the like, to surround or partially surround the desired target 5. In a wrapped orientation, the tubular member 400 may generally comprise an interior 420 of the tubular member formed by the wrapping of the body 410 into a wrapped position, one or more wrapped layers 430, and an exterior surface 440 of the tubular member 400 formed by the wrapping of the body 410 into a wrapped position. It is noted that the exterior surface 440 of the tubular member 400 may have a continuous "flat surface" as shown in FIG. 1, for example, or the exterior surface 440 of the tubular member 400 may have a "stepped surface" having a different number of layers as shown in FIGS. 2-4, for example.

In an embodiment, the first end 412 of the tubular body 400 may be opposite the second end 414 of the tubular member 400 on each side of the body 410. In an embodiment, the first end 412 may be approximately the same length as the second end 414. The first end 412 and the second end 414 may also correlate or refer to first and second sides, edges, or ends of the tubular member 400. In an embodiment, the first end 412 and the second end 414 may generally refer to the ends of the body 410 of the tubular member 400. In a wrapped position, the first end 412 and the second end 414 may generally refer to the open ends of the body 410 of the tubular member 400. The open ends, e.g., first and second ends 412, 414, may open into the interior 420 of the tubular member 400 and the open ends, e.g., first and second ends 412, 414, may be configured to receive a nerve, tendon, ligament, or the like therethrough.

In an embodiment, tubular member 400 or body 410 of the tubular member 400 may comprise an interior edge 416 and an exterior edge 418. In an embodiment, the interior edge 416 may be a different length than the exterior edge 418. In an embodiment, the interior edge 416 may have a longer length than a length of the exterior edge 418. The interior edge 416 and the exterior edge 418 may also correlate or refer to corresponding sides, edges, or ends of the tubular member 400. In an unwrapped orientation, the interior edge 416 may be opposite the one or more exterior edges 418. In a wrapped orientation, the interior edge 416 may be located in an interior (e.g., 420) of the tubular member 400 and the one or more exterior edges 418 may be located on an exterior (e.g., 440) of the tubular member 400. The interior 420 of the tubular member 400 and the interior edge 416 may be configured to receive or contact a nerve, tendon, ligament, or the like therethrough.

As shown in FIG. 4 opposite sides 412, 414 may have generally the same length and opposite edges 416, 418 may have a different length from each other. In an embodiment, interior edge 416 may extend from the first end 412 to the second end 414 of the tubular member 400. In an embodiment, exterior edge 418 may stop short of the first end 412 and/or the second end 414 of the tubular member 400. When in an unwrapped orientation, the tubular member 400 may resemble a trapezoidal shape. It is noted that other shapes are also disclosed and contemplated herein, including shapes having 3, 4, 5, 6, 7, etc. sides, shapes that have opposite sides of different lengths, shapes that are angled, shapes that have extended portions or irregular shapes, etc., for example, triangular, rectangular, diamond, parallelogram, and the like.

In an embodiment, the ends 412, 414 of the tubular member 400 may be flat, e.g., flat open ends. In an embodiment, a midline of the unwrapped sheet may generally align with or correspond to a midline of the wrapped tubular member 400. In an embodiment, each sequential wrap or layer of the tubular member 400 may align with the preceding wraps or layers. It is noted that other types of folds are wrapping are also disclosed and contemplated herein, including where each sequential wrap or layer is offset with preceding wraps or layers of the tubular member 400, where a midline of the unwrapped sheet may be offset from a midline of the wrapped tubular member 400, where the ends 412, 414 may not be flat or may be angled or tapered, etc. Due to the trapezoidal shape of the unwrapped tubular member 400, edges 412, 414 may form a flat end and may further extend onto the body 410 of the tubular member 400 (e.g., onto the exterior surface 440 of the tubular member 400) as a result of the decreasing length of the body 410 from the interior edge 416 to the exterior edge 418.

In an embodiment, the tubular member 400 many generally include three sections 452, 454, 456 that correspond to three separate sheets or three continuous sections of a single sheet (e.g., depending on whether multiple sheets or a single sheet are used respectively). It is noted that other any number of sections are also disclosed and contemplated herein, including 1, 2, 4, 5, 6, 7, etc. sections. Each section may provide or form an additional wrap or layer. For example, the wrap formed from section 452 may have x number of layers, the wrap formed from section 454 may have x+y number of layers, and the wrap formed from section 456 may have x+y+z number of layers. In an embodiment, section 452 (having the least layers) may correspond to the first and second ends 412, 414 of the tubular member or the outer portions of the tubular member 400 and section 456 (having the most layers) may correspond to a middle portion or area of the body 410 of the tubular member 400. Section 454 may be located on each side of section 456 and in between sections 452 and 456. In an embodiment, the number of layers 430 of the tubular member 400 may increase from the outer ends (e.g., ends 412, 414) of the tubular member 400 towards the middle of the body 410 of the tubular member 400 and may decrease from a middle of the body 410 of the tubular member 400 to the outer ends (e.g., ends 412, 414) of the tubular body 400.

In an embodiment, the body 410 and ends 412, 414 of the tubular member 400 may have different vertical cross-section across its length taken at sections 452, 454, 456. In an embodiment, the body 410 and ends 412, 414 of the tubular member 400 may have a different number of wraps or layers, e.g., 1, 2, 3, 4, 5, 6, etc. layers, at each section 452, 454, 456. In an embodiment, the body 410 and ends 412, 414 of the tubular member 400 may have a stepped outer surface 440 corresponding to sections 452, 454, 456. In an example, as shown in FIG. 4, the tubular member 400 may have all the same interior 420 diameter, a different number of layers 430 at sections 452, 454, 456, and the different exterior 440 diameter across a length of the tubular member 400, at sections 452, 454, 456.

For any of the tubular members 100, 200, 300, 400, 900, 1000, 1100 as herein described (as well as sheets 510, 600, etc. from which such tubes can be formed), it is noted that these tubular members may be provided as sheets (e.g., 510, 520 showing a rectangular shape) or as a conduit or pre-formed wrap (e.g., 530, 540 respectively). In an example, a rectangular wrap may have dimensions of 30 mm×40 mm. In an example, a conduit or preformed wrap may have an internal diameter of 6 mm and a length of 30 mm. In an example, the rectangular wrap size may range from and including 30 mm×20 mm up to and including 30 mm×60 mm. It is further noted that the each dimension of the rectangular wrap may range from and including 10.0 mm up to and including 80.0 mm. In an example, the conduit or preformed wrap may have an internal diameter range from and including 2 mm up to and including 8 mm, and may generally have the same length as the rectangular wrap, e.g. 30 mm. It is further noted that the conduit or preformed wrap may have an internal diameter range from and including 0.5 mm up to and including 10.0 mm, and may generally have the same length as the rectangular wrap, e.g. between 10.0 mm to 80.0 mm inclusive. Moreover, the tubular members 1000, 1100 may be include perforations, patterns, or may not include mesh or perforations or patterns, see perforated wrap 510, pattern 605, and non-perforated wrap 520.

Figure 6:
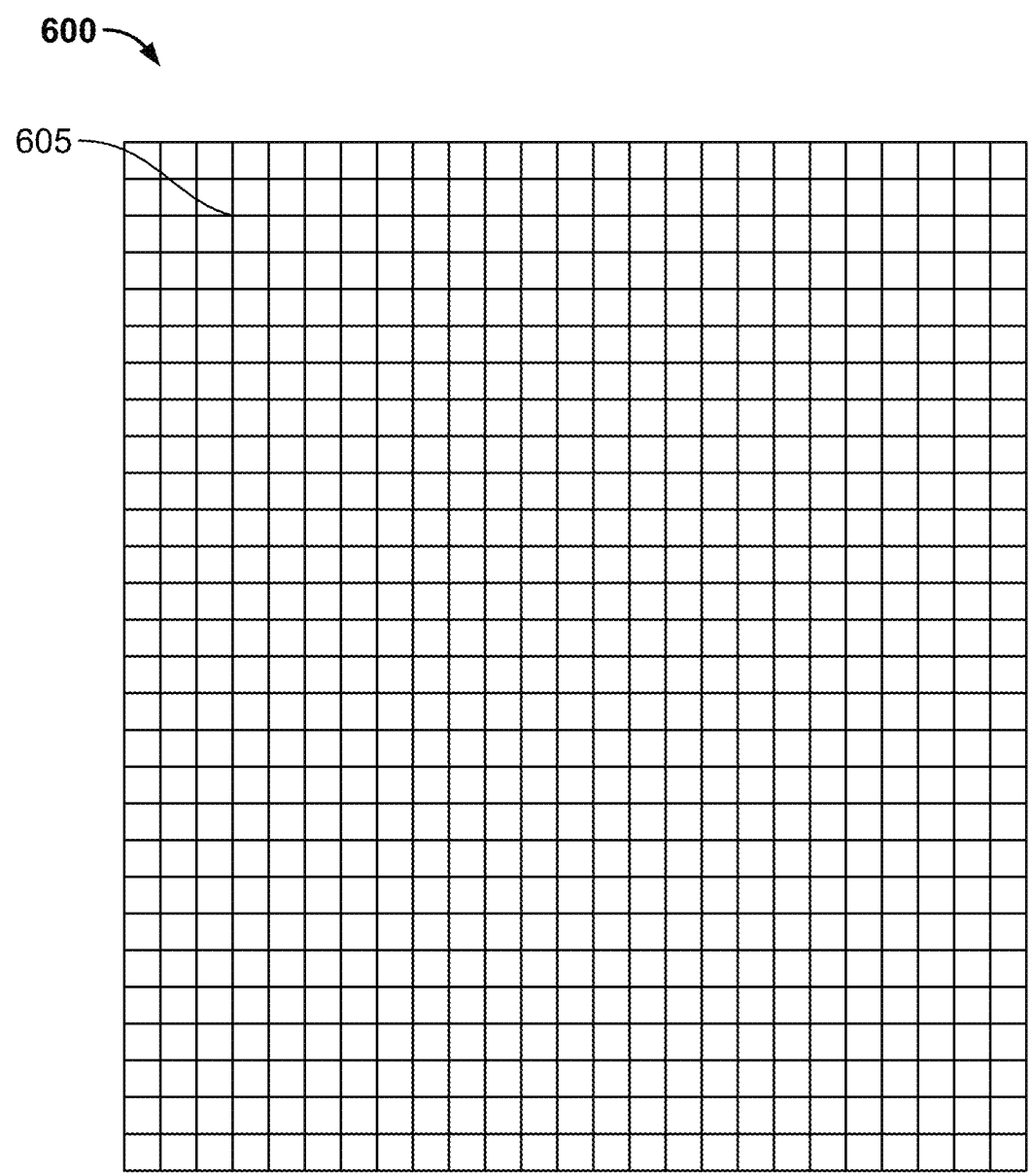
FIG. 6 is a top view of an embodiment of a delivery tool and/or exemplary patterning in accordance with this disclosure.

In an example, FIG. 6 shows sheet 600 having a pattern 605. Sheet 600 may having patterning 605 may be used as a tubular member or nerve wrap having patterning 605, may be used as a device to imprint or mold a pattern, such as patterning 605, onto a tubular member, or may be used as a delivery mechanism/tool (substrate to slide under) in conjunction with the tubular member. It is noted that the provided patterning 605 is an example and that any patterning may be used, including continuous or discontinuous patterning, patterning having more or less negative space, patterning resembling different shapes, such as lines curves, zig-zigs, circles, ovals, squares, rectangles, irregular shapes, asymmetrical or symmetrical shapes or patterning, and the like. Also see United States patent publication 2022/0218870, which is incorporated by reference.

Figure 8:
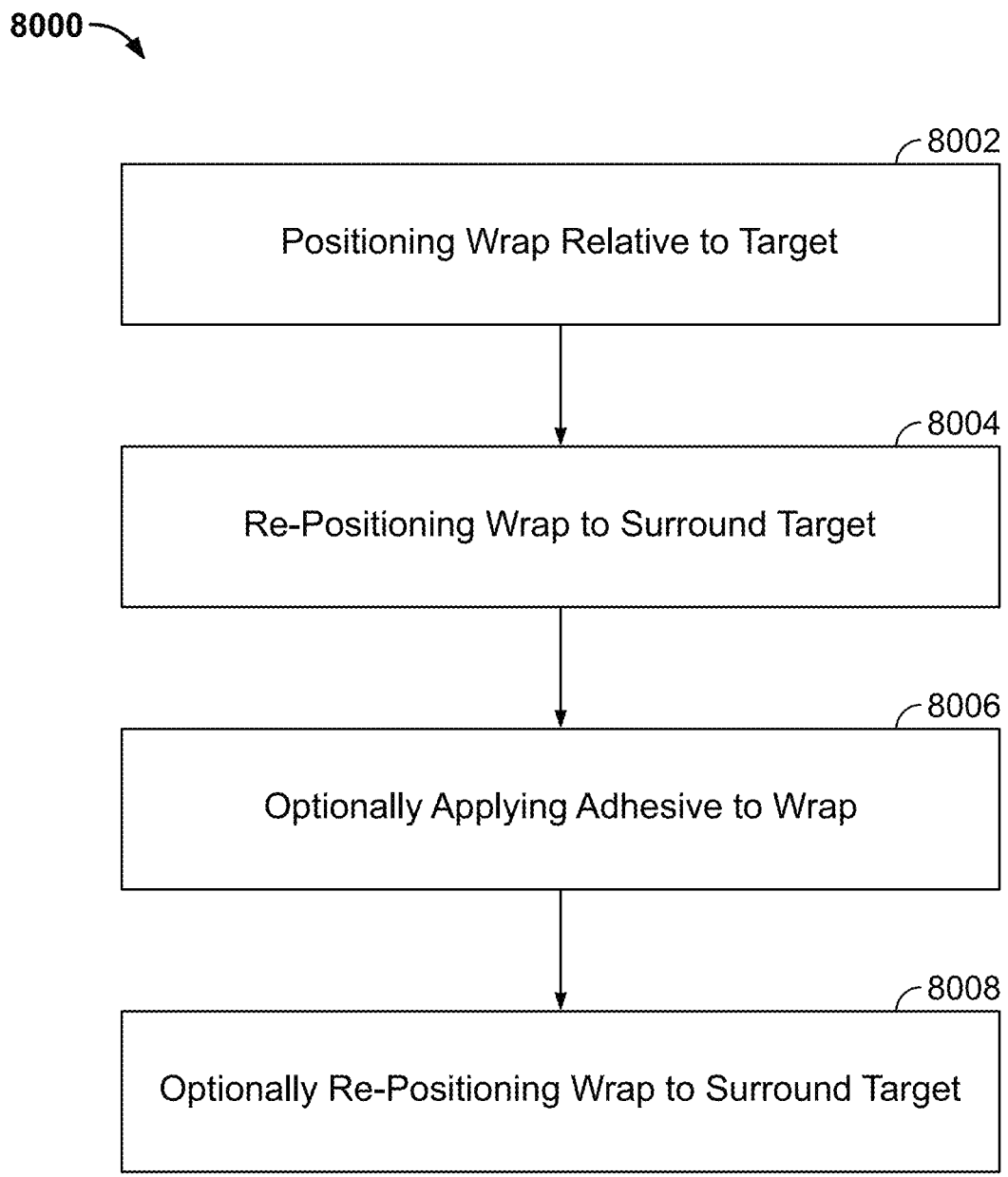
FIG. 8 is a schematic flowchart illustrating a method of applying a tubular member or nerve wrap to a target in accordance with this disclosure.

Turning to FIGS. 7-8, shown are methods of use that may be applied to form any of tubular members 100, 200, 300, 400, 900, 1000, 1100 from a sheet form as herein described, possibly as sheets 510, 600 or otherwise. Generally, a first method 7000 referred to as the burrito technique may include a step 7010 of placing the wrap/sheet underneath the target 5: a step 7020 of folding a first portion of the wrap over the top of the target 5: an optional step of applying a setting solution 705, adhesive, or other type of fastening element (e.g., stitches, etc.) onto the folded side of the wrap: and a step 7030 of folding a second portion of the wrap over the target 5 and the prior folded first portion. In an embodiment, the first folded portion may correspond to the interior edge of the tubular member and the second folded portion may correspond to the exterior edge of the tubular member. Second method 8000 further describes optional repositioning of the wrap to surround the target 5 as desired.

The present disclosure is not limited to the tubular shape described above, but may also comprise any of the following shapes-cone, frustoconical, reducing couplers, a combination of the foregoing or other like shapes. These shaped chitosan members may be formed from the chitosan sheet material and/or the chitosan strands that are wrapped or woven. By way of a non-limiting example, conical shapes can be formed via triangle sheets that are formed similar to the chitosan tube described above. Specifically, a triangle sheet of chitosan may be wrapped around a mandrel. The combination may be inserted into an optional forming shell. Next, the formed chitosan member of the applicable shape may be inserted into an alkaline aqueous medium containing at least one organic solvent. The organic solvent may comprise methanol, water and ammonia. In some embodiments, the chitosan member may be exposed to the alkaline solution for between one hour and forty-five minutes and two hours and fifteen minutes, e.g., about two hours. The chitosan member may be formed on an individual basis or as part of a larger bath where multiple chitosan members may be formed at one time.

Further still, the process may utilize different shapes and configurations that are similar to that of a nerve cuff or sleeve (e.g., oval, square, etc.). This may include an outer shape that is configured to fit within specific body parts or for specific uses where the shape could be beneficial. The present disclosure isn't limited to the shapes shown and disclosed, but instead any appropriate shape may be utilized and may be formed based on the methods described above.

The tube shape and other shapes identified above can alternatively be formed utilizing a layering approach. In these embodiments, small sheets of chitosan may be layered on top of each other to form the tube or applicably shaped chitosan device. In these embodiments, a chitosan device may be created with layering profiles by providing multiple sheets of chitosan over portions thereof to form different thicknesses. Once a first layer is put down, a solution of methanol, water, and acetic acid can be added to act as an adhering agent. Then a second layer may be laid or positioned over the first layer. The solution of methanol, water, and acetic acid may then be adhered to the second layer. A third layer of chitosan may then be placed over the second layer. This may be repeated for as many layers as needed to form the device, e.g., a number between 2 and 100. In these embodiments, these configurations may be artificially constrained in that the seam overlaps on all of these, e.g., layer 1, 2, and 3 can each be offset a few degrees axially.

In some embodiments, sheets of different thicknesses may be utilized in forming the final chitosan device, such as the chitosan tubes described above. These different thickness sheets may be layered in a predetermined pattern to form the shape of the applicable chitosan device, such as described above. In one embodiment, a thicker sheet may be used to form a butt-crimp.

In an embodiment, the chitosan tube may include piped ends, which are ends that are thicker than the remaining part thereof to provide a stronger area to adhere together. The middle may be thinner, which may allow dissolving on a target schedule. The ends of a chitosan tube may be thicker than the remaining portion thereof. The thicker ends may allow the clinician to differentiate the ends from the remaining parts of the chitosan tube. This may provide direction to the clinician as to where the ends are and make it easier for the clinician to suture such ends. The thicker end tubes may be formed as described above regarding chitosan sheets with thicker ends or may be formed as described above as a chitosan tube (any of the methods described above may be utilized) and then additional layers of chitosan (such as from smaller sheets or strands) may be added to the ends of the chitosan tube to form the chitosan tube with thicker end portions.

In an embodiment, a single sheet may be cut in different starting shapes and rolled into orientations that form different thicknesses over the tubular structure. An example is to utilize a trapezoid shaped sheet and then using the process above to create a device with a thicker wall at the center of the length and a thinner wall at the ends.

A chitosan device may utilize different thickness and dissolve rates based on the anatomy on which the device is used and/or the therapy. Specifically, one part of the device can dissolve faster than another part thereof. The device could also utilize different films with varying Degrees of Acetylation (DA) to force it to dissolve at different rates for different parts of the conduit geometry.

An embodiment may include a device (tube) with a closed end.

The chitosan devices 100, 200, 300, 400, 900, 1000, and 1100 may be made more visible, especially to a clinician, by coloring it. For example, a chitosan nerve guide may be colored, wherein during manufacture the chitosan is treated with a solution of a dye. In these embodiments, the chitosan device may be treated with a dye of any appropriate color, including, without limitation, red, green, blue, or black. This may help a clinician working with the device to see it in the body of the patient. In some embodiments, the chitosan device may be color coded based on the features it possesses. By way of a non-limiting example, if the chitosan device contains perforations, the perforated portion or even just the perforations may be colored in a color that is different from the remaining portion thereof. This may alert the user that the chitosan device is intended to be cut and can identify the location of where it can be cut. Further, the color coding can provide a location whereby in a product facility smaller sheets can be cut from larger sheets. In these embodiments, the color coding can provide a location by which the larger sheets can be cut to form the smaller sheets.

In some embodiments, the dye may be applied in a pattern, e.g., a stripe or checkerboard design. Further still, the dye may be applied in a graph pattern to make it easier to cut the chitosan device. The grid may provide lines of a predetermined distance from one another such that the clinician need only count the lines to know the applicable width or length of the chitosan device needed and use such lines to make applicable cuts. The lines may provide a guide to keep the cut-lines generally straight. This may essentially be like graph-paper lines on the chitosan device, see patterning 605 shown in FIG. 6, for example.

The pattern may be formed in any appropriate manner, including, without limitation via tint, print, patterns, and guides. In addition, the patterns may be formed on the chitosan device via laser etching, (especially on rounded surfaces) or laser or inkjet printing.

In an embodiment, the chitosan device may comprise different thicknesses. These different thicknesses may be used to form predetermined patterns on the device. Specifically, when the different thicknesses are exposed to a dye or tint, the dye or tint may end up being different colors because of the differences in thickness. For example, the thinner the portion of the chitosan device the darker the dye or tint may show. This may be utilized to create a predefined pattern on the device.

In an embodiment, the predefined pattern may be formed through use a process similar to engraving. This process may be used to create a pattern on the outer surface of the chitosan device.

Moreover, the chitosan device or portions thereof may be exposed to different color dyes or tints, which may result in different portions of the chitosan device being different colors. This exposure can create a predefined pattern in the chitosan device.

In an embodiment, the chitosan tubular member may have a corrugated configuration, i.e., a tubular member with corrugations through the entire length of the body of the tubular member or through a portion thereof, e.g., 20% to 100% of the length of the body. The corrugation configuration may allow the tube to bend such that it is able to end around areas within the body, which will help installation thereof. In an embodiment, the tube having a corrugated structure may facilitate bending around tissue.

The chitosan device 100, 200, 300, 400, 900, 1000, and 1100 may include packaging to aid and encourage a proper hydration technique for the chitosan device. One example will provide guidance to the clinician that the chitosan device requires a liquid bath before being used with a patient. Packaging examples include, but are not limited to, 1) placement in a thermoformed well so that hydration may occur in package as well as 2) including in that thermoformed well, a retention feature to allow hydration without curling.

Further, the hydration of the chitosan device may assist in positioning it in an operative position. For example, the chitosan device may utilize the curling that occurs during hydration to assist in positioning the device during a procedure. A tool of any appropriate configuration would be used to hold the chitosan device in an open position, either mechanically or using surface tension. The chitosan device may then be hydrated, which may cause the chitosan device to curl around a nerve to which it is to be attached. The un-hydrated chitosan device has a shape memory (e.g., tension or strain which drives return to original shape): once hydrated it will return to its original shape. This may help secure the chitosan device around a nerve and provide it in an operative fixation position whereby it can be fixed relative to the nerve.

In an embodiment, the shape memory of chitosan film based on different surface structures due to processing conditions, e.g., one side of the film takes up the water more quickly than the other side when hydrated so there is more vs. less swelling. These processing conditions may be used as a tool for manipulating the device and device shape when dehydrated and rehydrated. In case of conduits there may be an additional effect of the gluing in the curled position which adds to the "memory" of a curled design.

In one specific embodiment, a synthetic guide may consist of a hollow tubular body having woven or overlaid chitosan members spaced apart to create a mesh-like pattern. The synthetic guide may consist of one or more longitudinal constraining members positioned over the mesh-like pattern and opposing, radially aligned coupling strands, where the hollow tubular body, all of the longitudinal constraining members, and all of the coupling strands are configured to dissolve in between 1 and 21 months after the hollow tubular member is initially formed.

The following describe methods of delivery and retention of a chitosan tube into the target area as applied to the disclosures herein.

A chitosan device may include a separate fixation device or may include a fixation element that is a part of the chitosan device itself. In one embodiment, the fixation device, may comprise a different color than the rest of the chitosan device. This may allow a clinician to find the fixation device and differentiate it from the rest of the chitosan device. This way the clinician can easily find the fixation device or portion of the chitosan device and fix it to the patient in any appropriate way.

In one example, a first portion of a fixation portion, such as a lip, may be of a first color. A second portion of the fixation portion, such as a second lip, may be of a second color. Once the first fixation portion and second portion are positioned in a fixation position relative to one another, the first and second color may overlap to form a third color. For example, the chitosan device may include a first lip and second lip that are each of a different color, e.g., one may be yellow and the other blue. Once the first and second lips are positioned over each other to fix them together, they may create the appearance of a green color. This may let the clinician know that the first and second lips are in the appropriate position to be fixed together.

A tool of any appropriate configuration would be used to hold the chitosan device in an open position, either mechanically or using surface tension. In some embodiments, a smooth flexible background, for example made from silicone or TPE, may be used as a delivery tool. Alternatively, a membranous material, such as Tyvek, may be utilized as a backing material to aid delivery under and around the nerve.

The following describe methods of formation of a chitosan tube from a chitosan sheet as applied to the disclosures herein. The following methods of adhesion of chitosan films are additional methods of building a tube.

While suturing a wrap is the default method for maintaining the tubular fixation of the device around the targeted nerve, additional suture free methods may be used to maintain the tubular form after the wrap is applied to the nerve.

In one embodiment, an adhesive may be applied in advance in a strip on one face of the chitosan film, and the self-adhesive strip would then hold the wrap closed.

In an embodiment, shape memory of a chitosan sheet having the memory of a tube, but being provided in a flattened, sheet form, may provide formation of a tube without the need for additional adhesion.

In an embodiment, the interacting end surfaces of the wrapped tube may have corresponding structure to provide attachment between surfaces, e.g., corresponding protrusions and recesses, patterning, Ziploc-type configurations, etc.

In an embodiment, an adhesive (such as a fibrin glue) may be applied to the film during surgery to make it stick to itself and the target tissue to ensure that the wrap stays wrapped.

In an embodiment, a chemical setting solution such as acetic acid that partially dissolves the film (transforming to a hydrogel) may be temporarily applied to the film to enable self-adhesion. An additional solution to counteract the setting solution (e.g., an alkali to counteract or buffer the acid such as sodium citrate) may be applied to terminate further reaction of the film. In this two-solution method, dyes may be used to show that the two reagents have both been applied (for example, yellow and blue to make green).

Insofar as the foregoing embodiments contemplate tubular structures, these structures are understood to be hollow so as to accommodate and surround the nerve or tendon in need of repair. In this manner, the terms tube and tubular, rod, and cylinder and cylindrical may be used synonymously. Further, reference to longitudinal is synonymous with the axial direction of the cylinder, while transverse is synonymous with the radial direction. It will also be understood that, depending upon context, radial does not necessarily limit or require the cylinder to have a curved or circular cross section.

We claim:

1. A method of repairing a nerve or tendon comprising:
    forming a biodegradable sheet from a composition comprising chitosan, the composition configured to dissolve within 1 to 21 months after the biodegradable sheet is formed;
    wrapping the biodegradable sheet around a mandrel having a preselected size and shape to form a synthetic guide;
    disposing the synthetic guide around an injured nerve or tendon; and
    placing the mandrel wrapped with the biodegradable sheet in a forming shell, wherein the forming shell has a textured finish along interfaces where the forming shell comes into physical contact with the mandrel wrapped with the biodegradable sheet.

2. The method of claim 1 wherein the mandrel has a square or oval cross-sectional shape.

3. The method of claim 1 further comprising disposing the mandrel wrapped with the biodegradable sheet to an alkaline medium for a selected period of time.

4. The method of claim 3 wherein the alkaline medium comprises methanol, water, and ammonia.

5. The method of claim 1 wherein the forming shell includes axial sections configured to serve as couplers and/or reducers.

6. The method of claim 1 wherein the mandrel is formed from a plurality of components so that: i) the components are disposed around the injured nerve or tendon prior to wrapping the mandrel, and ii) the components are removed after the synthetic guide is formed.

7. The method of claim 1 wherein a plurality of biodegradable sheets are wrapped around the mandrel sequentially or simultaneously.

8. The method of claim 7 wherein a portion of one or more of the biodegradable sheets do not overlap so as to create comparatively thinner and thicker axial sections along a length of the synthetic guide.

9. The method of claim 1 wherein a single biodegradable sheet having a polygonal shape is wrapped around the mandrel so as to create comparatively thinner and thicker axial sections along a length of the synthetic guide.

10. The method of claim 9 wherein the polygonal shape is rectangular or trapezoidal.

11. The method of claim 1 wherein the biodegradable sheet is a solid sheet and further comprising the step of perforating the solid sheet to form a mesh pattern prior to wrapping the biodegradable sheet around the mandrel.

12. The method of claim 1 wherein the biodegradable sheet is formed from spaced apart fibers or strands configured to periodically overlap so as to create a mesh-like sheet.

13. The method of claim 12 wherein the mesh-like sheet is formed by weaving or overlaying the fibers or strands in a helical pattern around the mandrel.

14. The method of claim 1 further comprising disposing an adhering agent comprising methanol, water, and acetic acid onto the biodegradable sheet during or after the wrapping step.

15. The method of claim 1 further comprising folding or wrapping at least one axial section of the biodegradable sheet prior to forming the synthetic guide.

16. The method of claim 15 further comprising unfolding or unwrapping the axial section when the synthetic guide is disposed around an injured nerve or tendon so as to extend an axial length of the synthetic guide.

17. The method of claim 1 further comprising dying or etching at least a portion of the biodegradable sheet prior to forming the synthetic guide.

18. The method of claim 17 wherein the dying or etching includes creating a series of stripes, a grid, or a guide pattern to facilitate one or both of: wrapping the biodegradable sheet around the mandrel and disposing the synthetic guide around the injured nerve or tendon.

19. The method of claim 1 wherein the synthetic guide is formed free of use of sutures.

20. A synthetic guide consisting of:
    a hollow tubular body having woven or overlaid chitosan members spaced apart to create a mesh-like pattern;
    one or more longitudinal constraining members positioned over the mesh-like pattern;
    opposing, radially aligned coupling strands; and
    wherein the hollow tubular body, all of the longitudinal constraining members, and all of the coupling strands are configured to dissolve in between 1 and 21 months after the hollow tubular body is initially formed.

21. The synthetic guide of claim 20 wherein the chitosan members are fibers or strands.

22. The synthetic guide of claim 20 wherein the coupling strands consist of sutures.

23. The synthetic guide of claim 22 wherein the sutures are threaded through loops formed in at least one terminal end of each of the one or more longitudinal constraining members.

24. The synthetic guide of claim 20 wherein the hollow tubular body has a varied radial diameter or shape along an axial length of the hollow tubular body.

25. A synthetic guide comprising:
a hollow tubular member formed a biodegradable sheet comprising chitosan, said biodegradable sheet wrapped so as to overlap along at least an axially aligned portion of the hollow tubular member.

26. The synthetic guide of claim 25 wherein the synthetic guide does not include any sutures.

27. The synthetic guide of claim 25 wherein the hollow tubular member is formed from a plurality of biodegradable sheets, each biodegradable sheet including chitosan.

28. The synthetic guide claim 27 wherein the hollow tubular member includes a plurality of longitudinal sections and wherein at least two longitudinal sections have differing thicknesses.

29. The synthetic guide of claim 28 wherein there are at least three longitudinal sections, including two end sections and one midline section, and wherein the end sections have more layers than the midline section.

30. The synthetic guide of claim 28 wherein there are at least two longitudinal sections, including an end section and a midline section, and wherein the midline section has more layers than the end section.

31. The synthetic guide of claim 27 wherein at least two of the plurality of biodegradable sheets are adhered together with a composition comprising methanol, water, and acetic acid.

32. The synthetic guide of claim 25 wherein a single biodegradable sheet is used and wherein the hollow tubular member has a stepped surface.

33. The synthetic guide of claim 25 wherein the biodegradable sheet is folded or wrapped to impart variable thickness along discrete longitudinal sections of the hollow tubular member.

34. The synthetic guide of claim 25 wherein the biodegradable sheet is formed as a woven mesh or overlaid lattice of chitosan members, with the chitosan members spaced apart to define apertures in the hollow tubular member.

35. The synthetic guide of claim 34 further comprising longitudinal constraining members.

36. The synthetic guide of claim 35 further comprising coupling members attached to the constraining members at one or both ends of the hollow tubular member.

37. The synthetic guide of claim 25 wherein a plurality of polygonal biodegradable sheets are wound together to form the hollow tubular member.

38. The synthetic guide of claim 37 wherein at least two of the plurality of polygonal biodegradable sheets have different shapes.

39. The synthetic guide of claim 37 wherein at least two of the plurality of biodegradable sheets have different longitudinal sizes.

40. The synthetic guide of claim 25 wherein the synthetic guide is configured to dissolve in between 1 and 21 months after the hollow tubular member is initially formed.

41. The synthetic guide of claim 25 wherein the biodegradable sheet has a smooth surface except on an outermost exposed surface of the hollow tubular member, said outermost exposed surface having a textured finish.

42. A method of manufacturing a synthetic guide comprising chitosan, the method comprising:
preparing a liquid solution comprising a composition having chitosan;
applying the liquid solution onto a tubular rod so that the liquid solution adheres and solidifies around the tubular rod to form a hollow, tubular chitosan layer, thereby creating a synthetic guide; and
wherein the composition is configured to dissolve within 1 to 21 months after the hollow, tubular chitosan layer is initially formed, wherein a plurality of hollow tubular chitosan layers are formed by sequentially applying the liquid solution onto the tubular.

43. The method of claim 42 wherein at least portions of at least of the plurality of hollow, tubular chitosan layers overlap.

44. The method of claim 43 wherein the overlap creates a variable thickness along an axial length of the synthetic guide.

45. The method of claim 43 wherein the overlap creates a mesh-like structure including apertures in sidewalls of the hollow, tubular chitosan layer.

46. A method of manufacturing a synthetic guide comprising chitosan, the method comprising:
preparing a liquid solution comprising a composition having chitosan;
applying the liquid solution onto a tubular rod so that the liquid solution adheres and solidifies around the tubular rod to form a hollow, tubular chitosan layer, thereby creating a synthetic guide; and
wherein the composition is configured to dissolve within 1 to 21 months after the hollow, tubular chitosan layer is initially formed and wherein the tubular rod consists of a braided or woven support structure selected to adhere chitosan thereto.

47. A method of repairing a nerve or tendon comprising:
forming a biodegradable sheet from a composition comprising chitosan, the composition configured to dissolve within 1 to 21 months after the biodegradable sheet is formed;
wrapping the biodegradable sheet around a mandrel having a preselected size and shape to form a synthetic guide;
disposing the synthetic guide around an injured nerve or tendon; and
placing the mandrel wrapped with the biodegradable sheet in a forming shell, wherein the forming shell includes axial sections configured to serve as couplers and/or reducers.

48. A method of repairing a nerve or tendon comprising:
forming a biodegradable sheet from a composition comprising chitosan, the composition configured to dissolve within 1 to 21 months after the biodegradable sheet is formed;
wrapping the biodegradable sheet around a mandrel having a preselected size and shape to form a synthetic guide; and
disposing the synthetic guide around an injured nerve or tendon, wherein the mandrel is formed from a plurality of components so that: i) the components are disposed around the injured nerve or tendon prior to wrapping the mandrel, and ii) the components are removed after the synthetic guide is formed.

49. A method of repairing a nerve or tendon comprising:
forming a biodegradable sheet from a composition comprising chitosan, the composition configured to dissolve within 1 to 21 months after the biodegradable sheet is formed;
wrapping the biodegradable sheet around a mandrel having a preselected size and shape to form a synthetic guide; and
disposing the synthetic guide around an injured nerve or tendon, wherein a plurality of biodegradable sheets are wrapped around the mandrel sequentially or simultaneously and a portion of one or more of the biodegradable sheets do not overlap so as to create comparatively thinner and thicker axial sections along a length of the synthetic guide.

50. A method of repairing a nerve or tendon comprising:
forming a biodegradable sheet from a composition comprising chitosan, the composition configured to dissolve within 1 to 21 months after the biodegradable sheet is formed;
wrapping the biodegradable sheet around a mandrel having a preselected size and shape to form a synthetic guide; and
disposing the synthetic guide around an injured nerve or tendon, wherein a single biodegradable sheet having a polygonal shape is wrapped around the mandrel so as to create comparatively thinner and thicker axial sections along a length of the synthetic guide.

51. A method of repairing a nerve or tendon comprising:
forming a biodegradable sheet from a composition comprising chitosan, the composition configured to dissolve within 1 to 21 months after the biodegradable sheet is formed;
wrapping the biodegradable sheet around a mandrel having a preselected size and shape to form a synthetic guide; and
disposing the synthetic guide around an injured nerve or tendon wherein the biodegradable sheet is formed from spaced apart fibers or strands configured to periodically overlap so as to create a mesh-like sheet.

52. A method of repairing a nerve or tendon comprising:
forming a biodegradable sheet from a composition comprising chitosan, the composition configured to dissolve within 1 to 21 months after the biodegradable sheet is formed;
wrapping the biodegradable sheet around a mandrel having a preselected size and shape to form a synthetic guide;
disposing the synthetic guide around an injured nerve or tendon; and
disposing an adhering agent comprising methanol, water, and acetic acid onto the biodegradable sheet during or after the wrapping step.

53. A method of repairing a nerve or tendon comprising:
forming a biodegradable sheet from a composition comprising chitosan, the composition configured to dissolve within 1 to 21 months after the biodegradable sheet is formed;
wrapping the biodegradable sheet around a mandrel having a preselected size and shape to form a synthetic guide;
disposing the synthetic guide around an injured nerve or tendon;
folding or wrapping at least one axial section of the biodegradable sheet prior to forming the synthetic guide; and
unfolding or unwrapping the axial section when the synthetic guide is disposed around an injured nerve or tendon so as to extend an axial length of the synthetic guide.

54. A method of repairing a nerve or tendon comprising:
forming a biodegradable sheet from a composition comprising chitosan, the composition configured to dissolve within 1 to 21 months after the biodegradable sheet is formed;
wrapping the biodegradable sheet around a mandrel having a preselected size and shape to form a synthetic guide;
disposing the synthetic guide around an injured nerve or tendon; and
dying or etching at least a portion of the biodegradable sheet prior to forming the synthetic guide.

* * * * *